(12) United States Patent
Rentrop

(10) Patent No.: US 6,440,125 B1
(45) Date of Patent: Aug. 27, 2002

(54) EXCIMER LASER CATHETER

(76) Inventor: Peter Rentrop, 38 E. 22$^{nd}$ St., New York, NY (US) 10010

( * ) Notice: Subject to any disclaimer, the term of this patent is extended or adjusted under 35 U.S.C. 154(b) by 0 days.

(21) Appl. No.: 09/477,630

(22) Filed: Jan. 4, 2000

(51) Int. Cl.$^7$ ................................................ A61B 18/18
(52) U.S. Cl. ............................... 606/15; 606/7; 606/13; 606/14; 128/898
(58) Field of Search ..................... 606/3, 7, 8, 10–16; 607/88, 89; 128/898

(56) References Cited

U.S. PATENT DOCUMENTS

| | | |
|---|---|---|
| 4,641,912 A | 2/1987 | Goldenberg |
| 4,672,961 A | 6/1987 | Davies |
| 4,732,448 A | 3/1988 | Goldenberg |
| 4,770,653 A | 9/1988 | Shturman |
| 4,784,132 A | 11/1988 | Fox et al. |

(List continued on next page.)

FOREIGN PATENT DOCUMENTS

DE    29 23 633 A1 * 11/1997    ........ A61M/25/00

OTHER PUBLICATIONS

Excimer Laser Coronary Angioplasty by Frank Litvack, Neal L. Eigler and James S. Forrester.

*Primary Examiner*—Linda C. M. Dvorak
*Assistant Examiner*—Ahmed Farah
(74) *Attorney, Agent, or Firm*—Gibbons, Del Deo, Dolan, Griffinger & Vecchione

(57) ABSTRACT

A method and apparatus of providing endovascular therapy. The steps include arranging optical fibers within a catheter, the catheter having a tip whose length is at least 1 cm and whose diameter of less than 1 millimeter, connecting an excimer laser to the optical fibers; and delivering laser energy from the excimer laser in excess of 60 fluence at 40 Hertz through the optical fibers. The delivering of the laser energy may be to non-calcified or calcified deposits of an atherosclerotic lesion to ablate the same. The method also includes the step of inserting the catheter through an artery by pushing the same until the tip is in within laser energy striking distance of the atherosclerotic lesion.

16 Claims, 6 Drawing Sheets

U.S. PATENT DOCUMENTS

| | | | |
|---|---|---|---|
| 4,785,806 A | 11/1988 | Deckelbaum | |
| 4,799,754 A | 1/1989 | Goldenberg | |
| 4,830,460 A | 5/1989 | Goldenberg | |
| 4,844,062 A | 7/1989 | Wells | |
| 4,848,336 A | 7/1989 | Fox et al. | |
| 4,862,886 A | 9/1989 | Clarke et al. | |
| 4,905,689 A | 3/1990 | Stack et al. | |
| 4,917,084 A | 4/1990 | Sinofsky | |
| 4,950,266 A | 8/1990 | Sinofskyl | |
| 4,966,596 A | 10/1990 | Kunz et al. | |
| 5,005,180 A | 4/1991 | Edelman et al. | |
| 5,034,010 A | 7/1991 | Kittrell et al. | |
| 5,041,089 A | 8/1991 | Mueller et al. | |
| 5,041,108 A | 8/1991 | Fox et al. | |
| 5,044,717 A | 9/1991 | Levatter | |
| 5,061,265 A | 10/1991 | Abela et al. | |
| 5,109,859 A | 5/1992 | Jenkins | |
| 5,188,632 A | 2/1993 | Goldenberg | |
| 5,188,635 A | 2/1993 | Radttke | |
| 5,192,278 A * | 3/1993 | Hayes et al. | 606/15 |
| 5,196,004 A * | 3/1993 | Sinofsky | 606/3 |
| 5,217,456 A * | 6/1993 | Narciso, Jr. | 606/15 |
| 5,254,112 A | 10/1993 | Sinofsky et al. | |
| 5,312,396 A | 5/1994 | Feld et al. | |
| 5,334,207 A | 8/1994 | Gay, Jr. | |
| 5,350,375 A * | 9/1994 | Deckelbaum et al. | 606/7 |
| 5,429,604 A | 7/1995 | Hammersmark et al. | |
| 5,437,660 A * | 8/1995 | Johnson et al. | 606/15 |
| 5,456,680 A * | 10/1995 | Taylor et al. | 606/2 |
| 5,466,234 A * | 11/1995 | Loeb et al. | 606/15 |
| 5,470,330 A | 11/1995 | Goldenberg et al. | |
| 5,571,151 A | 11/1996 | Gregory | |
| 5,573,531 A | 11/1996 | Gregory | |
| 5,703,985 A * | 12/1997 | Owyang | 385/117 |
| 5,709,676 A | 1/1998 | Alt | |
| 5,722,972 A | 3/1998 | Power et al. | |
| 5,725,523 A | 3/1998 | Mueller | |
| 5,766,164 A | 6/1998 | Mueller et al. | |
| 5,807,384 A | 9/1998 | Mueller | |
| 5,817,144 A | 10/1998 | Gregory | |
| 5,843,033 A | 12/1998 | Ropiak | |
| 5,843,073 A | 12/1998 | Sinofsky | |
| 5,860,954 A | 1/1999 | Ropiak | |
| 5,873,366 A | 2/1999 | Chim et al. | |
| 5,891,133 A | 4/1999 | Murphy-Chutorian | |
| 5,916,210 A * | 6/1999 | Winston | 606/7 |
| 5,938,632 A | 8/1999 | Ellis | |

* cited by examiner

EXCIMER LASER CATHETER

CROSS-REFERENCE TO RELATED PATENT APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The invention relates to a catheter used to deliver laser energy from an excimer laser to a lesion within an arterial system or to a body organ. The catheter is particularly suited for use in endovascular therapy to ablate calcified or non-calcified deposits in atherosclerotic lesions.

2. Discussion of Related Art

U.S. Pat. Nos. 5,429,604 and 4,844,062 reveal that fiber optic catheter assemblies have increasingly been used for probing and clearing obstructions in various vessels such as arteries. The size of the vessel and the distance from the insertion point to the critical region in the vessel determine the characteristics of the catheter to be used. For example, in some situations it is desirable to insert a very thin catheter a considerable distance into a vessel. The catheter must be quite flexible so that it may be steered considerable distances through winding vessel passages.

The excimer laser enables the disintegration of targeted tissue and can yield relatively pure disintegration without excessive thermal damage to otherwise healthy tissue. The excimer laser is a combination of argon fluoride or krypton chloride and a rare earth gas. This combination forms a laser beam having a very short wavelength and hence photons of very high energy.

Excimer catheters for endovascular therapy are presently produced by the Spectranetics Corporation in the United States. Presently approved laser catheters in the United States for endovascular therapy range in diameter from 1.4 mm to 2.2 mm. The energy output for ablating atherosclerotic tissue in coronary or peripheral arteries is 60 fluence, 40 Hertz.

The ablation of atherosclerotic lesions by excimer laser energy transforms the lesions into water and carbon dioxide. A gas bubble forms at the laser catheter tip and expands rapidly, which stretches the vessel wall. The abrupt stretch can result in dissection and even occlusion of the vessel.

Calcium can not be ablated with commercially available catheters. Spectranetics has recently developed an excimer laser with more densely packed optical fibers, which results in a decrease of dead space and a higher energy output of 80 fluence or more, 40 Hertz or more. This recently developed excimer laser enables laser catheters to ablate calcium, but the higher energy output increases the likelihood of dissections. Also, existing laser catheters are relatively stiff, which precludes them from negotiating acute bends, which are common in arterial systems or in body organs.

It is desired that an excimer laser catheter be provided that is capable of being used to ablate hard, calcified areas and which may negotiate acute bends in the arterial system.

BRIEF SUMMARY OF THE INVENTION

One aspect of the invention resides in an apparatus and method for providing endovascular therapy. The apparatus includes an elongated catheter containing optical fibers arranged in a concentric manner, the catheter having a tip whose diameter is smaller than a remainder of the catheter, the tip having a length of at least 1 cm and a diameter of less than 1 millimeter. The apparatus preferably also includes an excimer laser connected to the optical fibers capable of delivering laser energy through the optical fibers. The method also includes the step of inserting the catheter through an artery by pushing the same until the tip is in within laser energy striking distance of a lesion for ablating the same. For treatment of heavily calcified lesions, the excimer laser should be capable of delivering laser energy at higher energy levels in excess of 60 fluence and in excess of 40 Hertz. For treatment of non-calcified lesions, the excimer laser need only be capable of delivering laser energy at lower energy levels, i.e., 60 fluence or less at 40 Hertz or less.

BRIEF DESCRIPTION OF THE SEVERAL VIEWS OF THE DRAWING

For a better understanding of the present invention, reference is made to the following description and accompanying drawings, while the scope of the invention is set forth in the appended claims.

DESCRIPTION OF THE INVENTION

Figure 1:
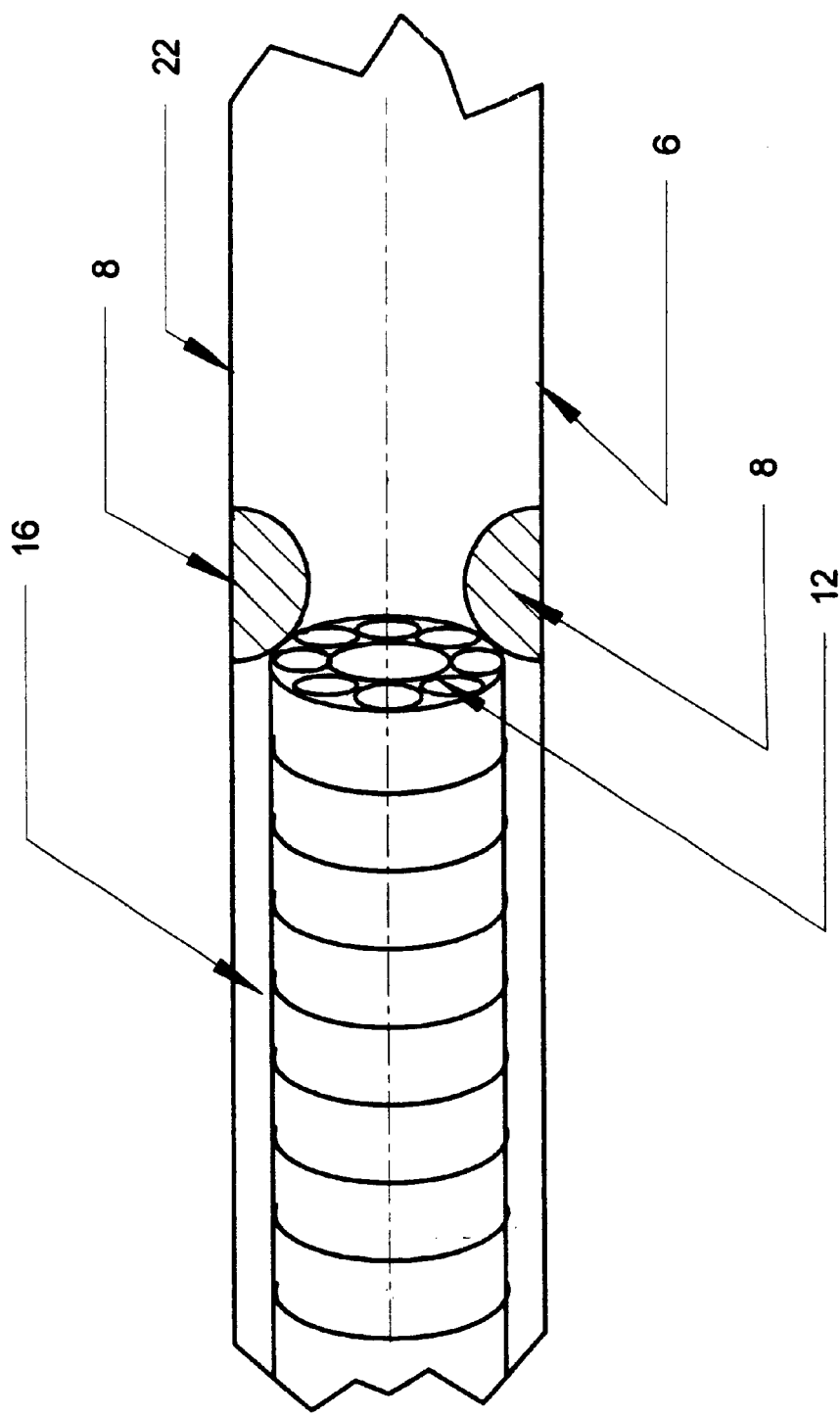
FIG. 1 is a schematic representation of a catheter tip segment in accordance with the invention that is in position to ablate atherosclerotic lesions.

Turning to FIG. 1, a coronary vessel 6 is shown having atherosclerotic blockage 8. A catheter contains optical fibers 12 and has a tip 16 that is inserted through the vessel 6 to reach the atherosclerotic blockage 8. An excimer laser that is connected to the catheter emits ultraviolet laser radiation energy through optical fibers 12. The laser radiation energy emerges from the catheter tip 16 to strike atherosclerotic blockage 8 to ablate the same.

The catheter tip 16 has a length of at least 1 centimeter and a diameter of less than 1 millimeter. Also, a guide wire 22 extends through a centerline of the catheter and is used in a conventional manner for guiding the catheter. Preferably, the tip length is at least 1 centimeter and up to 30 centimeters, although the optimal maximum length need only be as long as required for the catheter to come within laser striking distance of a lesion within the artery and traverse the lesion.

Presently available laser catheters that have tip diameters greater than 1 millimeter are unable to effectively ablate the calcium that is commonly present in atherosclerotic lesions. Experimental laser catheters have been developed that enable delivery of elevated laser energy levels that risk obtaining unwanted dissections. Dissections arise when the vessel wall stretches too much under stress from expanding gas bubbles that form at the tip of the laser catheter as the ablation of the atherosclerotic lesion transforms the lesion into water and carbon dioxide. Further, existing laser catheters are relatively stiff, which prevents them from negotiating acute bends common in the arterial systems.

By reducing the diameter of the catheter tip 16 to less than 1 millimeter, several advantages are realized. The smaller tip will cause less tissue to become vaporized per laser radiation emission. This results in a smaller gas bubble being formed than would otherwise be the case. The higher laser energy required to ablate calcium can be employed without increasing the likelihood of major dissections. In addition, the smaller tip is more effective for crossing heavily calcified lesions than are catheters having wider tips. Catheters having a tip diameter less than one millimeter are capable of crossing certain lesions that resist their crossing by wider diameter tip catheters. Furthermore, long lesions, which are not completely resistant to wider catheters, may be crossed with greater speed. That is, the use of the smaller catheter tip is more effective in crossing heavily calcified lesions than the use of the wider catheter tip.

By providing for a length of the catheter tip 16 to be at least one centimeter, additional advantages arise. One advantage resides in the tip 16 being more flexible because the diameter is smaller than for the wider conventional catheter tips. This greater flexibility enhances the ability of the laser catheter to negotiate bends within the arterial system, which often are present before reaching the lesion. That is, it enhances the likelihood of the laser catheter reaching the intended site of treatment. Another advantage is that the thinner tip enhances the likelihood of the laser catheter traversing severely calcified lesions that wider tips can not traverse.

A further advantage is that the catheter shaft is wider than the catheter tip 16 and thus readily pushable. Very thin catheters tend to store longitudinal energy when they are pushed forward over a guide wire 22. This reduces the ability to advance the tip 16. The thicker shaft of the present catheter is stiffer than the tip 16, which improves longitudinal energy transfer to the thin tip segment of the catheter. Thus, the present invention combines optimal pushability, because of the thicker shaft, with optimal flexibility, because of the thinner tip 16.

The use of a high energy miniaturized excimer laser may achieve the same luminal diameter as traditional lower energy laser catheters, because the relatively larger energy output of the miniaturized laser catheter should result in the formation of relatively larger gas bubbles. Gas bubble formation of a small high energy laser catheter may be comparable to that of a larger traditional energy laser catheter. Thus, the extent of vessel wall stretching may be comparable so the use of the miniaturized laser catheter is suited for calcified vessels of average and large diameter, in addition to being suited for small vessels.

In any size vessel over 2 millimeters in diameter that requires endovascular therapy, therefore, in which an excimer laser catheter is used to ablate calcified vessels, preferably a catheter tip segment of about at least 1 centimeter in length should be provided to have a diameter that is less than 1 millimeter. The catheter shaft, however, has a more conventional cross- sectional dimension that is larger than one millimeter. The use of high laser energy of more than 60 fluence and more than 40 Hertz has the specific goal of effectively treating heavily calcified lesions while the small tip dimension allows the high laser energy to be delivered without excessive gas bubble formation. Lower laser energy levels may be used such as 60 fluence at 40 Hertz to ablate holes through non-calcified tissue. A pilot hole was drilled through calcified tissue rapidly by emitting 2660 pulses of laser energy at 100 fluence/80 Hertz so the fastest and best results for ablating calcified tissue was for at least 80 fluence/80 Hertz excimer laser parameter settings.

The smaller tip segment (at least 1 cm in length) is flexible and enhances the ability to negotiate bends within the arterial system, affording better and easier access to the site of the lesion. Since the remainder of the catheter 14, i.e., the shaft, may be thicker and thus more rigid, the resulting device provides enhanced "push" and torque characteristics.

Figure 2:
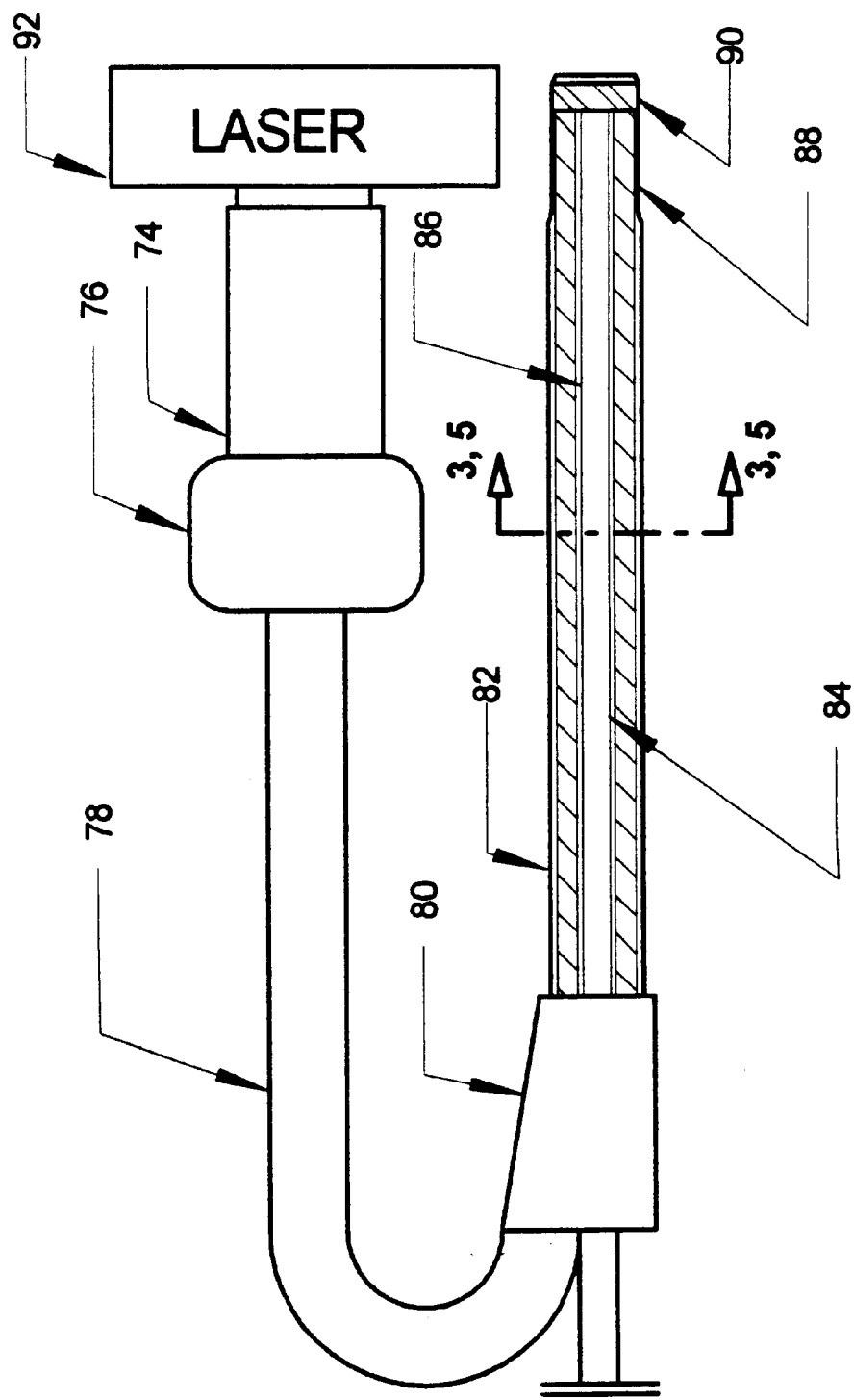
FIG. 2 is a schematic representation of a laser support catheter in accordance with the invention.
Figure 3:
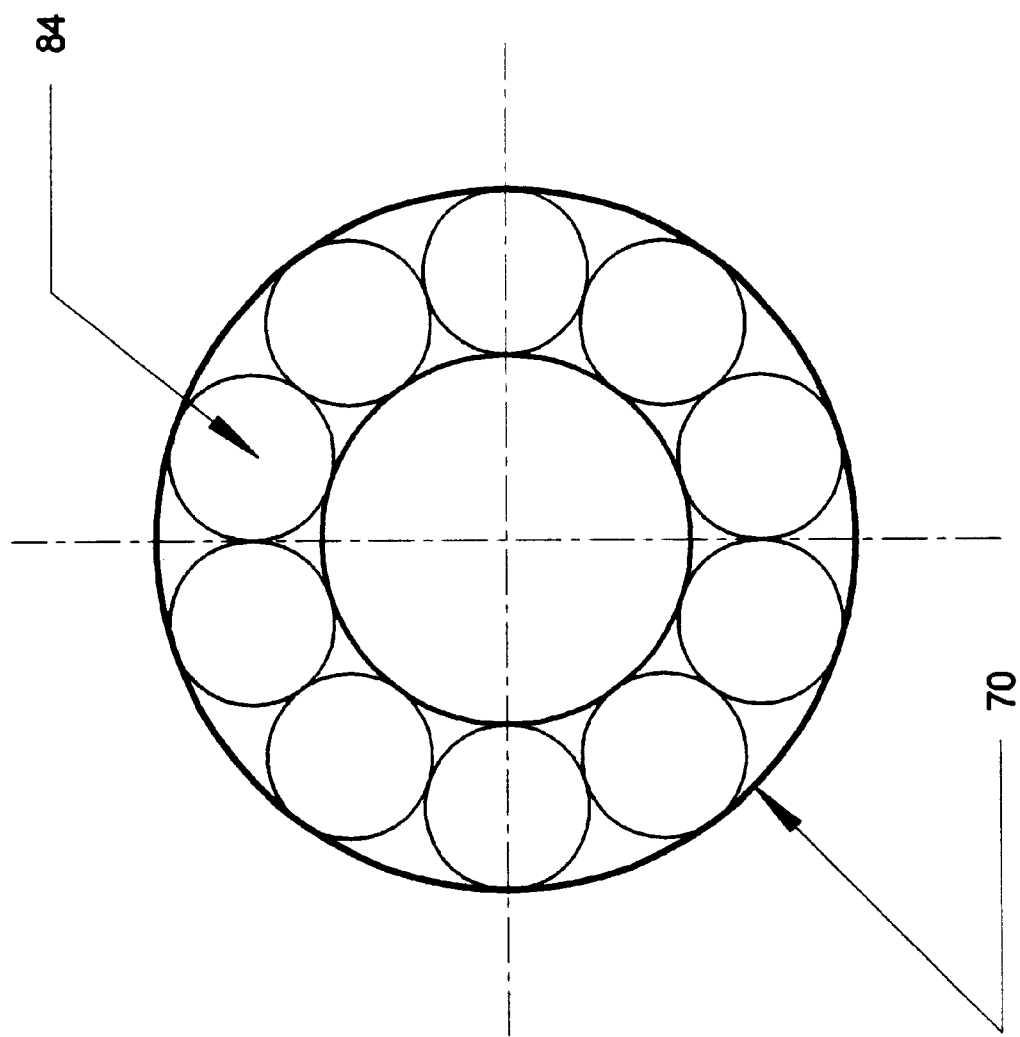
FIG. 3 is a cross-section taken from lines 3–3 of FIG. 2 in accordance with an embodiment using a single row of optical fibers.
Figure 4:
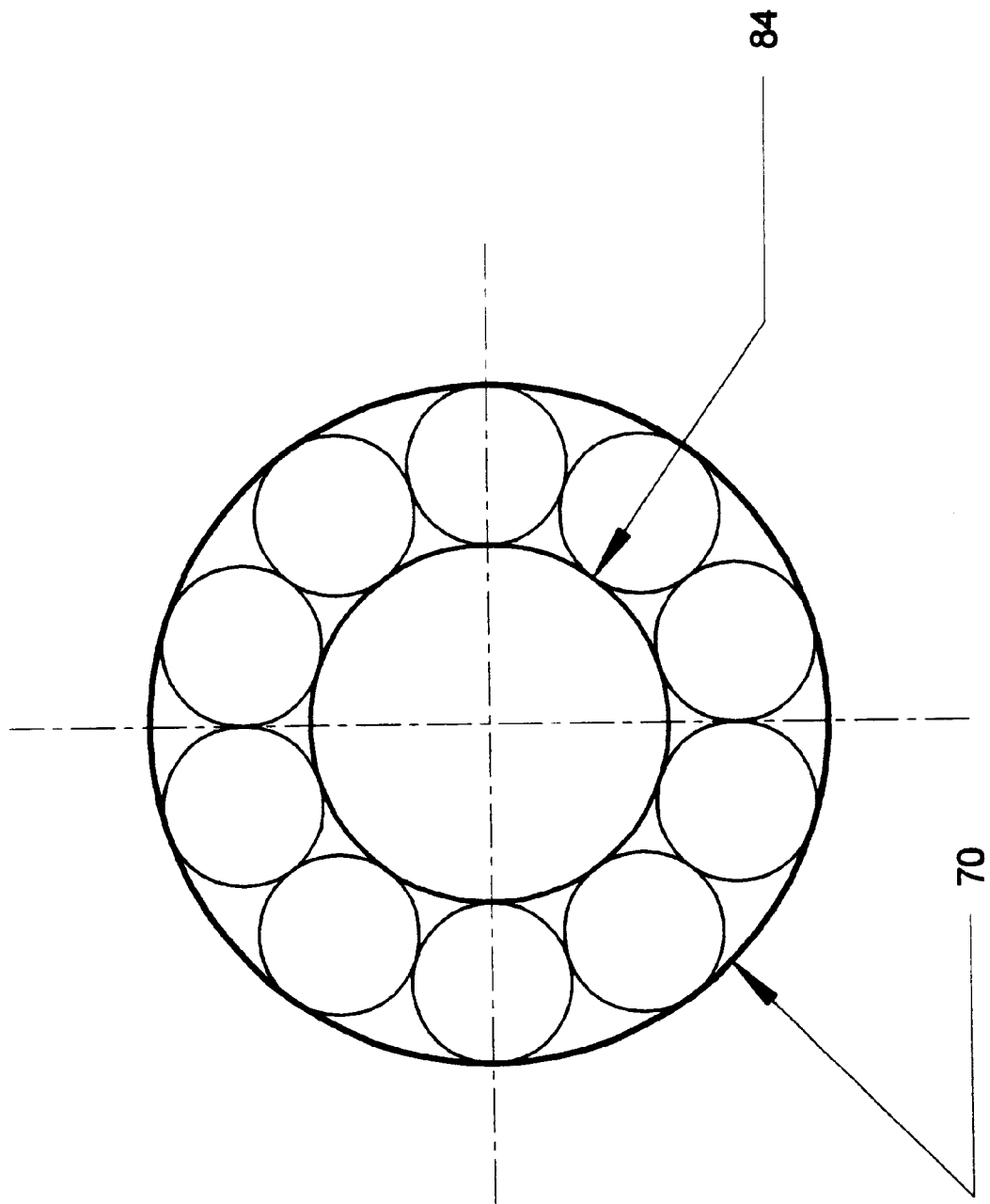
FIG. 4 is a distal end view of FIG. 2 for the embodiment of FIG. 3.
Figure 5:
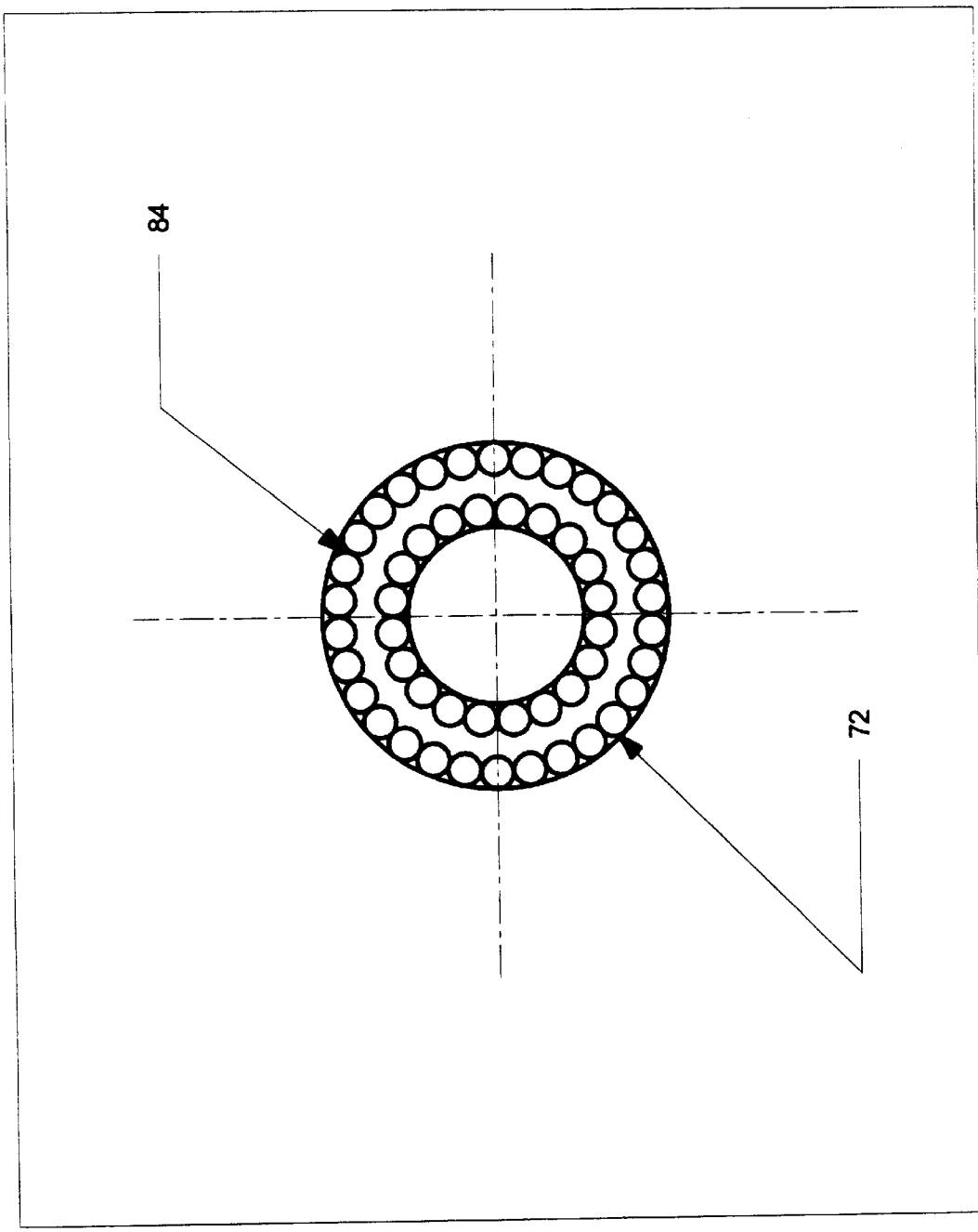
FIG. 5 is a cross-section taken from lines 5—5 of FIG. 2 in accordance with an embodiment using a double row of optical fibers.
Figure 6:
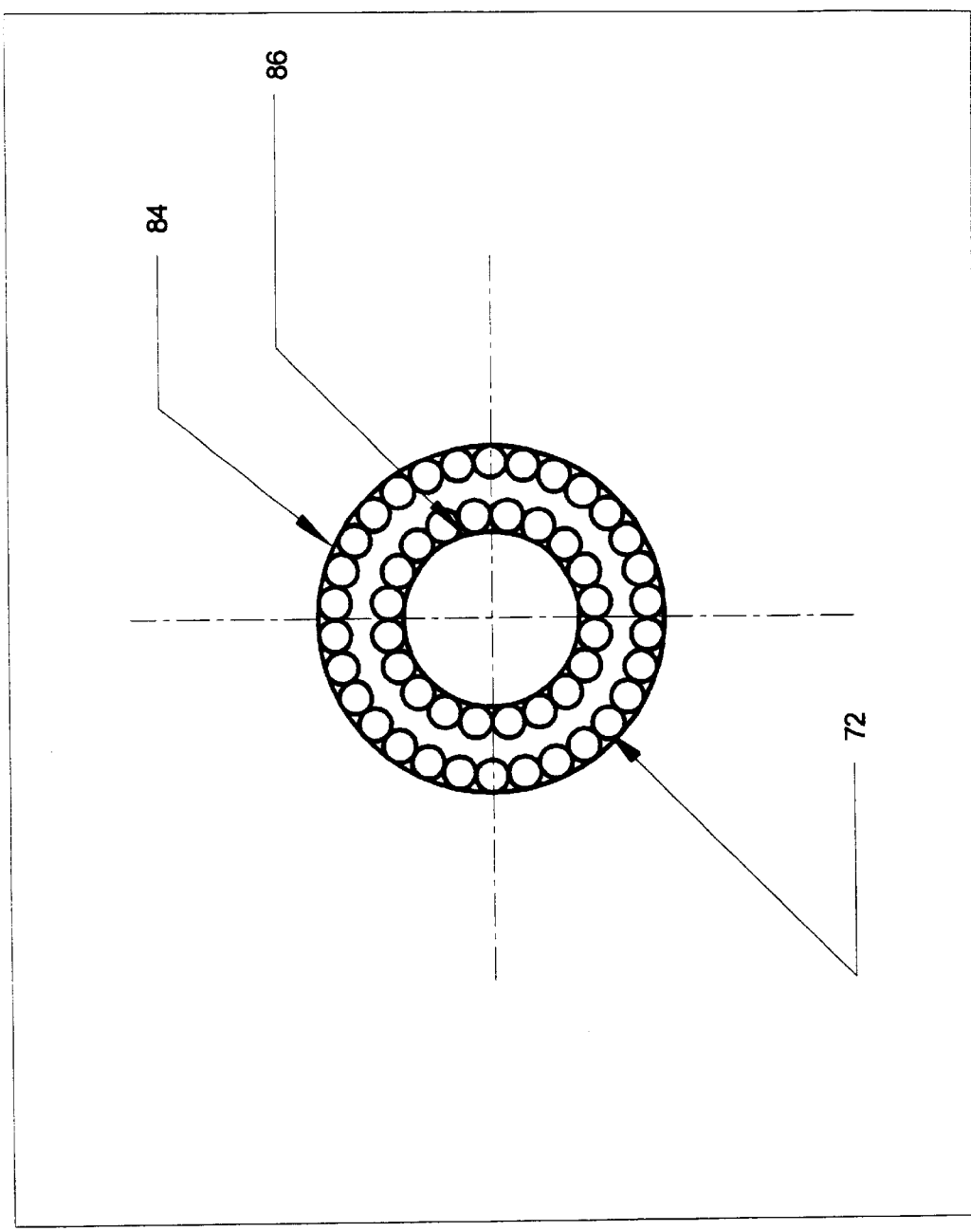
FIG. 6 is a distal end view of FIG. 3 for the embodiment of FIG. 5.

FIGS. 3–4 show a further embodiment of a single row laser support catheter 70 and FIGS. 5–6 show an additional embodiment of a double row laser support catheter 72. Both share the following conventional components depicted in FIG. 2: capillary tube 74, proximal coupler 76, tail tubing 78, bifurcate cover 80, proximal shaft 82, optical fibers 84 and an inner lumen 86. The proximal shaft 82 is preferably made of hytrel material. Also shown is a distal jacket 88 preferably made of hytrel material, a distal tip 90 preferably made of platinum and an excimer laser 92 (shown in box form). The main difference between the embodiments of FIGS. 3–4 and FIGS. 5–6 is that the embodiment of FIGS. 3–4 has a single row of optical fibers 84 concentrically arranged, while the embodiment of FIGS. 5–6 has two rows of optical fibers 84 concentrically arranged separated from each other radially.

With respect to the embodiment of FIGS. 3–4, a suitable optical fiber arrangement has 30 fibers each being a 45 to 50 micron fiber. With respect to the embodiment of FIGS. 5–6, a suitable optical fiber arrangement has 68 fibers each being a 45 to 50 micron fiber. The guide wire (not shown) has an internal diameter preferably of 0.014 to 0.016 inches. There are dimensional constraints on how small in diameter the catheter may be made. One constraint is the diameter of the optical fibers and the number of rows of optical fibers. While two rows are preferred for better consistent performance of laser energy delivery over that for just one single row, three rows may be used instead of just two rows to provide even better laser energy delivery performance. Of course, using three rows of optical fibers will make the catheter more densely packed and thus less flexible and more stiff than using two rows. Another constraint is the diameter of the guide wire and the wall thickness of the catheter, which must be taken into account for the dimension of the catheter. Taking all these dimensional constraints into consideration, the catheter preferably has a dimension of about 0.8 to 0.9 millimeters.

While the drawings show catheters that have a generally circular cross-section, the cross-section may instead be polygonal.

While the foregoing description and drawings represent the preferred embodiments of the present invention, it will be understood that various changes and modifications may be made without departing from the spirit and scope of the present invention.

What is claimed is:

1. An excimer laser catheter, comprising:
   an elongated body containing optical fibers in a concentric arrangement, the body having a tip whose diameter is smaller than a portion of a remainder of the body, the tip having a length of at least 1 cm and a diameter of at most 0.9 mm, the catheter being configured and arranged for being capable of delivering laser energy from an excimer laser through the optical fibers, each of the optical fibers extending through a full length of the tip.

2. A catheter as in claim 1, wherein the catheter is configured and arranged to deliver the laser energy at an energy level that is in excess of 60 fluence at 40 Hertz.

3. A catheter as in claim 1, wherein the optical fibers are arranged in at least two rows, spaced radially from each other and concentric with each other.

4. A catheter as in claim 1, wherein all of the optical fibers are arranged in a single row only and equidistant from a longitudinal axis of the body.

5. A catheter as in claim 1, wherein the optical fibers are arranged in only two rows, spaced radially from each other and concentric with each other.

6. A catheter as in claim 1, wherein the tip having an end made of platinum.

7. A catheter as in claim 1, wherein the tip has a diameter between about 0.8 mm and 0.9 mm, inclusive.

8. A method of providing endovascular therapy, comprising the steps of:

arranging within an elongated catheter a plurality of optical fibers in at least one row equidistant from a longitudinal axis of the elongated catheter, the catheter terminating in a tip whose length is at least 1 cm and a diameter of at most 0.9 mm, the optical fibers extending through a full length of the tip, the diameter of the tip being smaller than a diameter of a portion of a remainder of the catheter;

connecting an excimer laser to the optical fibers; and delivering laser energy from the excimer laser through the optical fibers.

9. A method as in claim 8, wherein the delivering of the laser energy is in excess of 60 fluence at 40 Hertz.

10. A method as in claim 8, wherein the step of arranging includes arranging the optical fibers in at least two rows spaced radially from each other and concentric with each other.

11. A method as in claim 8, wherein the step of arranging includes arranging all of the optical fibers in a single row and equidistant from a longitudinal axis of the catheter.

12. A method as in claim 8, wherein the step of arranging includes arranging the optical fibers in only two rows spaced radially from each other and concentric with each other.

13. A method as in claim 8, wherein the step of arranging includes providing an end of the tip that is made of platinum.

14. A method as in claim 8, further comprising forming the tip to have a diameter of between about 0.8 mm and 0.9 mm.

15. A method as in claim 8, further comprising the step of delivering the laser energy to calcified deposits of an atherosclerotic lesion.

16. A method as in claim 15, further comprising the step of inserting the catheter through an artery by pushing the same until the tip is in within laser energy striking distance of the atherosclerotic lesion for ablating the calcified deposits.

* * * * *

(12) EX PARTE REEXAMINATION CERTIFICATE (7294th)
United States Patent
Rentrop

(10) Number: US 6,440,125 C1
(45) Certificate Issued: Jan. 5, 2010

(54) EXCIMER LASER CATHETER

(76) Inventor: Peter Rentrop, 38 E. 22$^{nd}$ St., New York, NY (US) 10010

Reexamination Request:
No. 90/010,290, Sep. 19, 2008

Reexamination Certificate for:
Patent No.: 6,440,125
Issued: Aug. 27, 2002
Appl. No.: 09/477,630
Filed: Jan. 4, 2000

(51) Int. Cl.
*A61B 18/18* (2006.01)

(52) U.S. Cl. .............................. 606/15; 606/7; 606/13; 606/14; 128/898

(58) Field of Classification Search .................. None
See application file for complete search history.

(56) References Cited

U.S. PATENT DOCUMENTS

| | | | |
|---|---|---|---|
| 4,739,768 A | 4/1988 | Engelson | |
| 4,905,689 A | 3/1990 | Stack et al. | |
| 5,201,317 A | 4/1993 | Kanazawa et al. | 600/342 |
| 5,281,212 A | 1/1994 | Savage et al. | 606/15 |
| 5,415,653 A | 5/1995 | Wardle et al. | |
| 5,470,330 A | 11/1995 | Goldenberg et al. | |
| 5,514,128 A | 5/1996 | Hillsman et al. | |
| 6,117,128 A | 9/2000 | Gregory | 606/7 |
| 6,428,531 B1 | 8/2002 | Visuri et al. | 606/7 |
| 6,908,460 B2 | 6/2005 | DiStefano | 606/7 |

OTHER PUBLICATIONS

Appeal Record Page Nos. A00001–A00001. "Judgment entered Aug. 24, 2007".
Appeal Record Page Nos. A00002–A00022. "Memorandum and Order on Post–Verdict Motions dated Aug. 23, 2007".
Appeal Record Page Nos. A00023–A00053. "Findings of Fact and Conclusions of Law dated Aug. 23, 2007".
Appeal Record Page Nos. A00054–A00055. "Jury Verdict (Trial Tr., 1113:9–1118:15)".
Appeal Record Page Nos. A00056–A00063. "Order dated Aug. 2, 2005 denying Defendant's motion for summary judgment".
Appeal Record Page Nos. A00064–A00078. "Jury Instructions (Trial Tr., 1054:25–1106:22)".
Appeal Record Page Nos. A00079–A00095. "The entire docket sheet from proceedings below".
Appeal Record Page Nos. A00201–A00211. "Defendant's Trial Exh. No. A. U.S. Patent No. 6,440,125".
Appeal Record Page Nos. A00212–A00366. "Defendant's Trial Exh. No. B. U.S. Patent Office file history for the '125 patent".
Appeal Record Page Nos. A00367–A00520. "Defendant's Trial Exh. No. C. Cited references from the Patent Office file history for the '125 patent".
Appeal Record Page Nos. A00521–A00533. "Defendant's Trial Exh. No. D. U.S. Patent No. 6,673,064".
Appeal Record Page Nos. A00534–A00764. "Defendant's Trial Exh. No. E. U.S. Patent Office file history for the '064 patent".
Appeal Record Page Nos. A00765–A00853. "Defendant's Trial Exh. No. F. Cited references from the Patent Office file history for the '064 patent".

(Continued)

*Primary Examiner*—Beverly M. Flanagan

(57) ABSTRACT

A method and apparatus of providing endovascular therapy. The steps include arranging optical fibers within a catheter, the catheter having a tip whose length is at least 1 cm and whose diameter of less than 1 millimeter, connecting an excimer laser to the optical fibers; and delivering laser energy from the excimer laser in excess of 60 fluence at 40 Hertz through the optical fibers. The delivering of the laser energy may be to non-calcified or calcified deposits of an atherosclerotic lesion to ablate the same. The method also includes the step of inserting the catheter through an artery by pushing the same until the tip is in within laser energy striking distance of the atherosclerotic lesion.

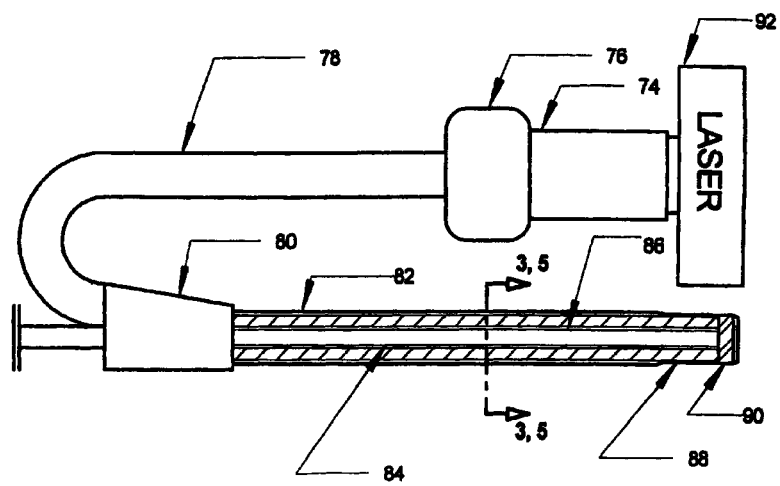

OTHER PUBLICATIONS

Appeal Record Page Nos. A00854–A00872. "Defendant's Trial Exh. No. G. Complaint filed by Dr Peter Rentrop in the Southern District of New York on Jan. 6, 2004".
Appeal Record Page Nos. A00873–A00911. "The Spectranetics Corporation's Answer, Affirmative Defenses, and Counterclaims".
Appeal Record Page Nos. A00912–A00933. "Defendant's Trial Exh. No. H. The Spectranetics Corporation's First Amended Answer, Affirmative Defenses, and Counterclaims.".
Appeal Record Page Nos. A00934–A00945. "Dr. Rentrop's Reply to First Amended Counterclaims".
Appeal Record Page Nos. A00946–A01386. "Defendant The Spectranetics Corporation's Motion for Summary Judgment, Brief in Support, Statement Pursuant to Local Rule 56.1, and exhibits".
Appeal Record Page Nos. A01387–A01416. "Plaintiffs Opposition to Defendant The Spectranetics Corporation's Motion for Summary Judgment, Brief in Support, Rule 56.1 Statement, and exhibits".
Appeal Record Page Nos. A01417–A01785. "Defendant The Spectranetics Corporation's Reply Brief in Further Support of Its Motion for Summary Judgment, Reply Statement Pursuant to Local Rule 56.1, and exhibits".
Appeal Record Page Nos. A01786–A01804. "Trial Transcript: Nov. 27, 2006 (pp. 1–75)".
Appeal Record Page Nos. A01805–A01846. "Trial Transcript: Nov. 28, 2006 (pp. 76–239)".
Appeal Record Page Nos. A01847–A01889. "Trial Transcript: Nov. 29, 2006 (pp. 240–412)".
Appeal Record Page Nos. A01890–A01935. "Trial Transcript: Nov. 30, 2006 (pp. 41 3–596)".
Appeal Record Page Nos. A01936–A01977. "Trial Transcript: Dec. 4, 2005 (pp. 597–762)".
Appeal Record Page Nos. A01978–A02026. "Trial Transcript: Dec. 5, 2006 (pp. 763–958)".
Appeal Record Page Nos. A02179–A02216. "Trial Transcript: Dec. 7, 2006 (pp. 959–1110)".
Appeal Record Page Nos. A02217–A02219. "Trial Transcript: Dec. 8, 2006 (pp. 1111–1122)".
Appeal Record Page Nos. A02220–A02242. "Defendant's Trial Exh. No. I. Complaint filed by The Spectranetics Corporation on Jul. 22, 2003 in the United States District Court for the District of Colorado".
Appeal Record Page Nos. A02243–A02249. "Defendant's Trial Exh. No. J. Declaration of Dr. Peter Rentrop in support of Rentrop'Motion to Dismiss the Complaint in the District Court of Colorado".
Appeal Record Page Nos. A02250–A02266. "Defendant's Trial Exh. No. K. Order dated Jan. 26, 2004 of Judge Figa granting Rentrop's Motion to Dismiss the Complaint in Colorado".
Appeal Record Page Nos. A02267–A02287. "Defendant's Trial Exh. No. L. Plaintiff's Response to Defendant's Second Set of Interrogatories to Plaintiff (Nos. 8–16)".
Appeal Record Page Nos. A02288–A02295. "Defendant's Trial Exh. No. M. Plaintiff's Response to Defendant's Second Set of Requests for Production of Documents and Things to Plaintiff (No. 20)".
Appeal Record Page Nos. A02296–A02299. "Defendant's Trial Exh. No. N. Confidentiality Agreement Jan. 21, 1999 between Spectranetics and Dr. Rentrop".
Appeal Record Page Nos. A02300–A02304. "Defendant's Trial Exh. No. O. Letter dated Aug. 14, 2000 from Guy Childs to Dr. Rentrop with the signed confidentiality agreement".
Appeal Record Page Nos. A02305–A02305. "Defendant's Trial Exh. No. P. Letter dated Sep. 23, 2002 from Dr. Rentrop to Bruce Ross".
Appeal Record Page Nos. A02306–A02320. "Defendant's Trial Exh. No. Q. Letter dated Jul. 9, 2003 from Robert Hess to John Schulte".
Appeal Record Page Nos. A02321–A02322. "Defendant's Trial Exh. No. R. Letter dated Mar. 30, 1998 from Kevin Taylor to Dr. Rentrop".
Appeal Record Page Nos. A02323–A02326. "Defendant's Trial Exh. No. S. Letter dated Apr. 17, 1989 from Kevin Taylor to Dr. Rentrop attaching three catheter designs".
Appeal Record Page Nos. A02327–A02330. "Defendant's Trial Exh. No. T. Letter dated Apr. 20, 1998 from Kevin Taylor to Dr. Rentrop".
Appeal Record Page Nos. A02331–A02331. "Defendant's Trial Exh. No. U. Letter dated Apr. 30, 1998 from Kevin Taylor to Dr. Rentrop".
Appeal Record Page Nos. A02332–A02332. "Defendant's Trial Exh. No. V. Letter dated May 21, 1998 from Kevin Taylor to Dr. Rentrop".
Appeal Record Page Nos. A02333–A02333. "Defendant's Trial Exh. No. W. Letter dated May 21, 1998 from Kevin Taylor to Dr. Rentrop".
Appeal Record Page Nos. A02334–A02334. "Defendant's Trial Exh. No. X. Letter dated Aug. 12, 1998 from Kevin Taylor to Dr. Rentrop".
Appeal Record Page Nos. A02335–A02336. "Defendant's Trial Exh. No. Y. Letter dated Sep. 2, 1998 from Ken Harlan to Dr. Rentrop".
Appeal Record Page Nos. A02337–A02337. "Defendant's Trial Exh. No. Z. Letter dated Sep. 9, 1998 from Dr. Rentrop to Kevin Taylor".
Appeal Record Page Nos. A02338–A02338 "Defendant's Trial Exh. No. A1. Memorandum dated Oct. 19, 1998 from Kevin Taylor to Chris Reiser".
Appeal Record Page Nos. A02339–A02340 "Defendant's Trial Exh. No. B1. Letter dated Jan. 20, 1999 from Kevin Taylor to Dr. Rentrop".
Appeal Record Page Nos. A02341–A02342 "Defendant's Trial Exh No. C1. Letter dated Jan. 21, 1999 from Kevin Taylor to Dr. Rentrop".
Appeal Record Page Nos. A02343–A02343 "Defendant's Trial Exh. No. D1. Letter dated Dec. 2, 1998 from William Kerker to Dr. Rentrop".
Appeal Record Page Nos. A02344–A02344 "Defendant's Trial Exh. No. E1. Memorandum dated Jan. 25, 1999 from Bill Kerker to Kevin Taylor".
Appeal Record Page Nos. A02345–A02345 "Defendant's Trial Exh. No. F1. Letter dated Jan. 28, 1999 from Joseph Largey to Dr. Rentrop".
Appeal Record Page Nos. A02346–A02350 "Defendant's Trial Exh. No. G1. Letter dated Feb. 12, 1999 from Kevin Taylor to Dr. Rentrop".
Appeal Record Page Nos. A02351–A02352 "Defendant's Trial Exh. No. H1. Letter dated May 12, 1999 from Kevin Taylor to Dr. Hilton".
Appeal Record Page Nos. A02353–A02353 "Defendant's Trial Exh. No. I1. Memo dated Oct. 19, 1998 from Chris Reiser to Kevin Taylor".

Appeal Record Page Nos. A02354–A02354 "Defendant's Trial Exh. No. J1. Memo dated Mar. 2, 1999 from Dan Bossie to Jim McCluskey".
Appeal Record Page Nos. A02355–A02355 "Defendant's Trial Exh. No. K1. Memo dated Mar. 2, 1999 from Dan Bossie to Chris Reiser".
Appeal Record Page Nos. A02356–A02356 "Defendant's Trial Exh. No. L1. Memo dated Mar. 4, 1999 from Dan Bossie to Chris Reiser".
Appeal Record Page Nos. A02357–A02363 "Defendant's Trail Exh. No. M1. Agreement signed by Dr. Rentrop dated Jul. 8, 1999 directed to Kevin Taylor".
Appeal Record Page Nos. A02364–A02371 "Defendant's Trial Exh. No. N1. Draft terms and conditions dated Aug. 26, 1999".
Appeal Record Page Nos. A02372–A02372 "Defendant's Trial Exh. No. O1. Letter dated Aug. 31, 1999 from Guy Childs to Dr. Rentrop".
Appeal Record Page Nos. A02373–A02373 "Defendant's Trial Exh. No. P1. Letter dated Jul. 28, 2000 from Guy Childs to Dr. Rentrop".
Appeal Record Page Nos. A02374–A02380 "Defendant's Trial Exh. No. Q1. Project Performance Report by Ken Harlan dated Jan. 10, 2002".
Appeal Record Page Nos. A02381–A02389 "Defendant's Trial Exh. No. R1. Extreme OTW 0.9 mm X80 Laser Catheters (Jul. 2003)".
Appeal Record Page Nos. A02390–A02395 "Defendant's Trial Exh. No. S1. Extreme Laser Catheters (Sep. 2003)".
Appeal Record Page Nos. A02396–A0241 "Defendant's Trial Exh. No. T1. Percutaneous Excimer Laser Coronary Angioplasty (ELCA)—Vitesse XTO Laser Catheter (Mar. 23, 2000)".
Appeal Record Page Nos. A02402–A02410 "Defendant's Trial Exh. No. U1. Vitesse–C Catheters (Jun. 2003)".
Appeal Record Page Nos. A02411–A02411 "Defendant's Trial Exh. No. V1. Project Report from Ken Harlan dated Apr. 7, 1998".
Appeal Record Page Nos. A02412–A02412 "Defendant's Trial Exh. No. W1. Project Report from Ken Harlan dated Apr. 14, 1998".
Appeal Record Page Nos. A02413–A02413 "Defendant's Trial Exh. No. X1. Project Report from Ken Harlan dated Apr. 21, 1998".
Appeal Record Page Nos. A02414–A02414 "Defendant's Trial Exh. No. Y1. Project Report from Ken Harlan dated Apr. 28, 1998".
Appeal Record Page Nos. A02415–A02415 "Defendant's Trial Exh. No. Z1. Project Report from Ken Harlan dated May 12, 1998".
Appeal Record Page Nos. A02416–A02416 "Defendant's Trial Exh. No. A2. Project Report from Ken Harlan dated May 5, 1998".
Appeal Record Page Nos. A02417–A02417 "Defendant's Trial Exh. No. B2. Project Report from Ken Harlan dated May 19, 1998".
Appeal Record Page Nos. A02418–A02418 "Defendant's Trial Exh. No. C2. Project Report from Ken Harlan dated May 26, 1998".
Appeal Record Page Nos. A02419–A02419 "Defendant's Trial Exh. No. D2. Project Report from Ken Harlan dated Jun. 23, 1998".
Appeal Record Page Nos. A02420–A02420 "Defendant's Trial Exh. No. E2. Project Report from Ken Harlan dated Jun. 30, 1998".
Appeal Record Page Nos. A02421–A02421 "Defendant's Trial Exh. No. F2. Page 11 of Product Bulletin 7030–0286–00 dated Jun. 1, 1998".
Appeal Record Page Nos. A02422–A02423 "Defendant's Trial Exh. No. G2. Drawing dated Mar. 30, 1998".
Appeal Record Page Nos. A02424–A02425 "Defendant's Trial Exh. No. H2. Drawing of 0.014 Laser Support Catheter".
Appeal Record Page Nos. A02426–A02427 "Defendant's Trial Exh. No. I2. Drawing of 0.018 Laser Support Catheter".
Appeal Record Page Nos. A02428–A02429 "Defendant's Trial Exh. No. J2. Drawing of Catheter".
Appeal Record Page Nos. A02430–A02437 "Defendant's Trial Exh. No. K2. Next Generation Catheters for Excimer Laser Coronary Angioplasty by Kevin Taylor and Chris Reiser, Lasers Med. Sci. 2001 16:133–140".
Appeal Record Page Nos. A02438–A02456 "Defendant's Trial Exh. No. L2. Small Excimer Laser Angioplasty Catheter for Fibrocalcific Tissue Penetration by Kevin Taylor, Ken Harlan, et al."
Appeal Record Page Nos. A02457–A02466 "Defendant's Triah Exh. No. M2. Memo to Operating Committee Peripheral Catheter Task Team dated May 7, 1992".
Appeal Record Page Nos. A02467–A02493 "Defendant's Trial Exh. No. N2. Preliminary Design Review Peripheral Laser Wire dated May 14, 1992".
Appeal Record Page Nos. A02494–A02501 "Defendant'Trial Exh. No. O2. Employment Agreement for Kevin Taylor dated Mar. 26, 1992".
Appeal Record Page Nos. A02502–A02509 "Defendant's Trial Exh. No. P2. Employment Agreement for Ken Harlan dated May 8, 1992".
Appeal Record Page Nos. A02510–A02510 "Defendant's Trial Exh. No. Q2. Drawing dated Apr. 6, 1992".
Appeal Record Page Nos. A02511–02511 "Defendant's Trial Exh. No. Q2. Blowup of drawing dated Apr. 6, 1992 with Markings by Reiser".
Appeal Record Page Nos. A02512–A02512 "Defendant's Trial Exh. No. R2. Product Bulletin for 1.2 mm Laserprime Catheter".
Appeal Record Page Nos. A02513–A02513 "Defendant's Trial Exh. No. S2. U.S. Patent No. 5,514,128 of Cecily Hillsman and Kevin Taylor for "Fiber Optic Guide Wire and Support Catheter Therefor" dated May 7, 1996".
Appeal Record Page Nos. A02532–A02549 "Defendant's Trial Exh. No. T2. U.S. Patent No. 5,643,251 of Cecily Hillsman and Kevin Taylor for "Fiber Optic Guide Wire and Support Catheter Therefor" dated Jul. 1, 1997".
Appeal Record Page Nos. A02550–A02550 "Defendant's Trial Exh. No. U2. Drawing of Prima 0.018".
Appeal Record Page Nos. A02551–A02551 "Defendant's Trial Exh. No. V2. Drawing dated Jan. 9, 1998 of Prima 0.018 Laserwire".
Appeal Record Page Nos. A02552–A02569 "Defendant's Trial Exh. No. W2. Protocol for 0.018 Prima dated Jul. 16, 1997".
Appeal Record Page Nos. A02570–A02576 "Defendant's Trial Exh. No. X2. Drawings of support catheter assembly by Kevin Taylor dated in 1993".

Appeal Record Page Nos. A02577–A02577 "Defendant's Trial Exh. No. Y2. Drawing of catheter assembly by Kevin Taylor dated Sep. 7, 1994".

Appeal Record Page Nos. A02578–A02581 "Defendant's Trial Exh. No. Z2. Spectranetics test results to Ken Harlan, Chris Reiser, and Kevin Taylor dated Apr. 12, 1996".

Appeal Record Page Nos. A02582–A02592 "Defendant's Trial Exh. No. A3. U.S. Patent No. 5,263,952 to Kenneth Grace et al. for "Two–Piece Tip for Fiber Optic Catheter" dated Nov. 23, 1993".

Appeal Record Page Nos. A02593–A02605 "Defendant's Trial Exh. No. B3. U.S. Patent No. 5,429,617 to Hammersmark et al. for "Radiopaque Tip Marker for Alignment of a Catheter within a Body" dated Jul. 4, 1995".

Appeal Record Page Nos. A02606–A02610 "Defendant's Trial Exh. No. C3. Nonocclusive Excimer Laser–Assisted End–to–Side Anastomosis by Tulleken et al, The Society of Thoracic Surgeons dated 1997".

Appeal Record Page Nos. A02611–A02616 "Defendant's Trial Exh. No. D3. The Modified Excimer Laser–Assisted High–Flow Bypass Operation by Tulleken et al, Elsevier Science Inc. dated 1996".

Appeal Record Page Nos. A02617–A02628 "Defendant's Trial Exh. No. E3. Rentrop's German Patent 2923633 dated Dec. 18, 1980".

Appeal Record Page Nos. A02629–A02635 "Defendant's Trial Exh. No. F3. Certified Translation of Rentrop's German Patent".

Appeal Record Page Nos. A02636–A02640 "Defendant's Trial Exh. No. G3. Infusion Catheter Catalog dated Jan. '82, '86, '89, '90".

Appeal Record Page Nos. A02641–A02641 "Defendant's Trial Exh. No. H3. Comparison between Figure 2 of the '064 and '125 patents and the drawing prepared by Kevin Taylor".

Appeal Record Page Nos. A02642–A02643 "Defendant's Trial Exh. No. L3. Demonstrative Chart of Prior Art—Figures 14 and 11 B of Taylor's '251 Patent".

Appeal Record Page Nos. A02644–A02647 "Defendant's Trial Exh. No. M3. Portion of Transcript of Apr. 29, 2005 Markman Hearing".

Appeal Record Page Nos. A02648–A02650 "Defendant's Trial Exh. No. O3. Monthly Report dated May 4, 1994 from Kevin Taylor to Chris Reiser".

Appeal Record Page Nos. A02651–A02653 "Defendant's Trial Exh. No. P3. Monthly Report dated Jun. 6, 1994 from Kevin Taylor to Chris Reiser".

Appeal Record Page Nos. A02654–A02663 "Defendant's Trial Exh. No. Q3. R&D Project Priority Meeting Notes dated Jul. 19, 1994 from Chris Reiser".

Appeal Record Page Nos. A02664–A02664 "Defendant's Trial Exh. No. R3. Notes dated Aug. 15, 1994 by Chris Reiser".

Appeal Record Page Nos. A02665–A02665 "Defendant's Trial Exh. No. S3. Demonstrative Drawing similar to Page 3 of Spectranetics' Reply Brief in Support of its Motion for Summary Judgment (Color–coded Tip of Spectranetics Catheter)".

Appeal Record Page Nos. A02666–A02668 "Defendant's Trial Exh. No. U3. Physical samples of the accused laser catheters".

Appeal Record Page Nos. A02669–A02671 "Defendant's Trial Exh. No. V3. Physical samples of the AIS 1 .3Z Excimer Laser Catheter".

Appeal Record Page Nos. A02672–A02716 "Defendant's Trial Exh. No. W3. Physical samples of Prima Laserwire with Catheter Support Shaft (including Instructions for Use)".

Appeal Record Page Nos. A02721–A02722 "Defendant's Trial Exh. No. Y3. Page 7 of Robert Golobic's Product Development Notebook dated Mar. 16, 1986".

Appeal Record Page Nos. A02733–A02737 "Defendant's Trial Exh. No. A4. U.S. Patent No. 5,415,653 dated May 16, 1995 to Wardle et al."

Appeal Record Page Nos. A02738–A02752 "Defendant's Trial Exh. No. B4. U.S. Pat. No. 5,423,806 dated Jun. 13, 1995 to Dale et al."

Appeal Record Page Nos. A02753–A02765 "Defendant's Trial Exh. No. C4. U.S. Patent No. 5,429,617 dated Jul. 4, 1995 to Hammersmark et al."

Appeal Record Page Nos. A02766–A02802 "Defendant's Trial Exh. No. D4. U.S. Pat. No. 5,470,330 dated Nov. 28, 1995 to Goldenberg et al."

Appeal Record Page Nos. A02803–A02804 "Defendant's Trial Exh. No. E4. Springs firm develops surgical laser to battle heart disease, Gazette Telegraph, dated Mar. 27, 1988".

Appeal Record Page Nos. A02805–A02839 "Defendant's Trial Exh. No. H4. U.S. Patent Office File History for U.S. Appl. No. 10/751,785".

Appeal Record Page Nos. A02840–A02849 "Defendant's Trial Exh. No. I4. Physical Samples of the 1.4 Catheter".

Appeal Record Page Nos. A02850–A02850 "Defendant's Trial Exh. No. J4. Drawing of 1.4 Extreme Catheter (Dwg. No. 3650–0175)".

Appeal Record Page Nos. A02851–A02851 "Defendant's Trial Exh. No. K4. Drawing of 1.4 Vitesse Catheter (Dwg. No. 3650–0417)".

Appeal Record Page Nos. A02852–A02852 "Defendant's Trial Exh. No. L4. Drawing of .9 80/80 Extreme Catheter (Dwg. No. 3650–1278)".

Appeal Record Page Nos. A02853–A02853 "Defendant's Trial Exh. No. M4. Drawing of .9 80/80 Vitesse Catheter (Dwg. No. 3650–1280)".

Appeal Record Page Nos. A02854–A02854 "Defendant's Trial Exh. No. P4. Blowup of Figs. 1 and 2 of '064 Patent".

Appeal Record Page Nos. A02855–A02855 "Defendant's Trial Exh. No. S4. Drawing by Reiser of Labeled Transverse Cross–Section of Prima system".

Appeal Record Page Nos. A02856–A02856 "Defendant's Trial Exh. No. T4. Drawing by Reiser of Labeled Longitudinal Cross–Section of Prima system".

Appeal Record Page Nos. A02857–A02857 "Defendant's Trial Exh. No. U4. Spectranetics' Licenses Demonstrative".

Appeal Record Page Nos. A02858–A02858 "Defendant's Trial Exh. No. V4. Reasonable Royalty Summary Demonstrative".

Appeal Record Page Nos. A02859–A02872 "Plaintiff's Trial Exh. No. PX–1. Certified copy of U.S. Patent No. 6,673, 064".

Appeal Record Page Nos. A02873–A03835 "Plaintiff's Trial Exh. No. PX–2. '064 Patent Prosecution History and all the Cited References".

Appeal Record Page Nos. A03881–A03892 "Plaintiff's Trial Exh. No. PX–3. Certified copy of U.S. Patent 6,440,125".

Appeal Record Page Nos. A03892.01–A03892.0450 "Plaintiff's Trial Exh. No. PX–4. 125 Patent Prosecution History".

Appeal Record Page Nos. A03901–A03912 "Plaintiff's Trial Exh. No. PX–9. Dr. Rentrop's German Patent application # DE2923633A1".
Appeal Record Page Nos. A03913–A03917 "Plaintiff's Trial Exh. No. PX–10. Infusion Catheter Catalog".
Appeal Record Page Nos. A03918–A03926 "Plaintiff's Trial Exh. No. PX–11. Pharamacologic and Mechanical Interventions in Ischemic Heart Disease: A Two–Day Course".
Appeal Record Page Nos. A03927–A03939 "Plaintiff's Trial Exh. No. PX–11. Interventions in the Treatment of Heart Disease: A Three–Day Course".
Appeal Record Page Nos. A03940–A03948 "Plaintiff's Trial Exh. No. PX–11. Interventions in the Treatment of Heart Disease".
Appeal Record Page Nos. A03949–A03955 "Plaintiff's Trial Exh. No. PX–11. Interventions in the Treatment of Heart Disease".
Appeal Record Page Nos. A03956–A03962 "Plaintiff's Trial Exh. No. PX–11. Interventions in the Treatment of Heart Disease: A Two–Day Course".
Appeal Record Page Nos. A03963–A03969 "Plaintiff's Trial Exh. No. PX–11. Interventions in the Treatment of Heart Disease: A Two–Day Course".
Appeal Record Page Nos. A03970–A03971 "Plaintiff's Trial Exh. No. PX–12. Memos from Kos".
Appeal Record Page Nos. A03972–A03972 "Plaintiff's Trial Exh. No. PX–12. Letter from Kerker to Rentrop".
Appeal Record Page Nos. A03973–A03974 "Plaintiff's Trial Exh. No. PX–12. Memo from Kerker".
Appeal Record Page Nos. A03975–A03976 "Plaintiff's Trial Exh. No. PX–12. Memo from Kerker to Kos".
Appeal Record Page Nos. A03977–A03977 "Plaintiff's Trial Exh. No. PX–12. Letter from Kerker to Rentrop".
Appeal Record Page Nos. A03978–A03978 "Plaintiff's Trial Exh. No. PX–13. Taylor Daytimer Entry".
Appeal Record Page Nos. A03979–A03980 "Plaintiff's Trial Exh. No. PX–14. Taylor Daytimer Entry".
Appeal Record Page Nos. A03981–A03981 "Plaintiff's Trial Exh. No. PX–15. Taylor Daytimer Entry".
Appeal Record Page Nos. A03982–A03983 "Plaintiff's Trial Exh. No. PX–16. Taylor Daytimer Entry".
Appeal Record Page Nos. A03984–A03985 "Plaintiff's Trial Exh. No. PX–17. Taylor Daytimer Entry".
Appeal Record Page Nos. A03986–A03986 "Plaintiff's Trial Exh. No. PX–18. Taylor Daytimer Entry".
Appeal Record Page Nos. A03987–A03988 "Plaintiff's Trial Exh. No. PX–19. Letter from Taylor to Dr. Rentrop re: Henk Kos".
Appeal Record Page Nos. A03989–A03990 "Plaintiff's Trial Exh. No. PX–20. Taylor Daytimer Entry".
Appeal Record Page Nos. A03991–A03991 "Plaintiff's Trial Exh. No. PX–21. Taylor Daytimer Entry".
Appeal Record Page Nos. A03992–A03993 "Plaintiff's Trial Exh. No. PX–22. Taylor Daytimer Entry".
Appeal Record Page Nos. A03994–A03995 "Plaintiff's Trial Exh. No. PX–23. Taylor Daytimer Entry".
Appeal Record Page Nos. A03996–A03996 "Plaintiff's Trial Exh. No. PX–24. Taylor Daytimer Entry".
Appeal Record Page Nos. A03997–A04000 "Plaintiff's Trial Exh. No. PX–25. Letter from Taylor to Dr. Rentrop re: Catheter Designs".
Appeal Record Page Nos. A04001–A04001 "Plaintiff's Trial Exh. No. PX–26. 0.018 Laser Support Catheter Drawing".
Appeal Record Page Nos. A04002–A04003 "Plaintiff's Trial Exh. No. PX–27. Taylor Daytimer Entry".
Appeal Record Page Nos. A04004–A04007 "Plaintiff's Trial Exh. No. PX–28. Letter from Taylor to Dr. Rentrop re: Invention Disclosure".
Appeal Record Page Nos. A04008–A04009 "Plaintiff's Trial Exh. No. PX–29. Taylor Daytimer Entry".
Appeal Record Page Nos. A04010–A04010 "Plaintiff's Trial Exh. No. PX–30. Letter from Taylor to Dr. Rentrop re: Catheter Prototypes".
Appeal Record Page Nos. A04011–A04012 "Plaintiff's Trial Exh. No. PX–31. Taylor Daytimer Entry".
Appeal Record Page Nos. A04013–A04013 "Plaintiff's Trial Exh. No. PX–32. Harlan Daytimer Entry".
Appeal Record Page Nos. A04014–A04017 "Plaintiff's Trial Exh. No. PX–33. Harlan Lab Notebook Entry".
Appeal Record Page Nos. A04018–A04018 "Plaintiff's Trial Exh. No. PX–34. Letter from Taylor to Dr. Rentrop re: 0.014 Laser Catheter".
Appeal Record Page Nos. A04019–A04020 "Plaintiff's Trial Exh. No. PX–35. Taylor Daytimer Entry".
Appeal Record Page Nos. A04021–A04025 "Plaintiff's Trial Exh. No. PX–36. Letter from Taylor to Dr. Rentrop re: Confidentiality Agreement".
Appeal Record Page Nos. A04026–A04029 "Plaintiff's Trial Exh. No. PX–37. Confidentiality Agreement".
Appeal Record Page Nos. A04030–A04031 "Plaintiff's Trial Exh. No. PX–38. Taylor Daytimer Entry".
Appeal Record Page Nos. A04032–A04032 "Plaintiff's Trial Exh. No. PX–39. Harlan Daytimer Entry".
Appeal Record Page Nos. A04033–A04033 "Plaintiff's Trial Exh. No. PX–40. Harlan Lab Notebook Entry".
Appeal Record Page Nos. A04034–A04035 "Plaintiff's Trial Exh. No. PX–41. Harlan Lab Notebook Entry".
Appeal Record Page Nos. A04044–A04044 "Plaintiff's Trial Exh. No. PX–42. Letter from Taylor to Dr. Rentrop re: 3 Catheters".
Appeal Record Page Nos. A04045–A04046 "Plaintiff's Trial Exh. No. PX–43. Taylor Daytimer Entry".
Appeal Record Page Nos. A04047–A04048 "Plaintiff's Trial Exh. No. PX–44. 0.014 XTO Device".
Appeal Record Page Nos. A04049–A04050 "Project Goals and Strategies".
Appeal Record Page Nos. A04051–A04052 "Plaintiff's Trial Exh. No. PX–45. Taylor Daytimer Entry".
Appeal Record Page Nos. A04053–A04053 "Plaintiff's Trial Exh. No. PX–46. Taylor Daytimer Entry".
Appeal Record Page Nos. A04054–A04055 "Plaintiff's Trial Exh. No. PX–47. Letter from Harlan to Dr. Rentrop re: Demo Prima .018" SX".
Appeal Record Page Nos. A04056–A04056 "Plaintiff's Trial Exh. No. PX–48. Letter from Dr. Rentrop to Taylor re: Solving Torque Problem".
Appeal Record Page Nos. A04057–A04058 "Plaintiff's Trial Exh. No. PX–49. Taylor Daytimer Entry".
Appeal Record Page Nos. A04059–A04059 "Plaintiff's Trial Exh. No. PX–50. Taylor Daytimer Entry".
Appeal Record Page Nos. A04060–A04060 "Plaintiff's Trial Exh. No. PX–51. Letter from Don Bossie to Dr. Rentrop re: Points Discussed".
Appeal Record Page Nos. A04061–A04062 "Plaintiff's Trial Exh. No. PX–52. Taylor Daytimer Entry".
Appeal Record Page Nos. A04063–A04063 "Plaintiff's Trial Exh. No. PX–53. Harlan Daytimer Entry".

Appeal Record Page Nos. A04064–A04064 "Plaintiff's Trial Exh. No. PX–54. Email from Reiser to Taylor re: Compensation for Dr. Rentrop".

Appeal Record Page Nos. A04065–A04065 "Plaintiff's Trial Exh. No. PX–55. Email from Bossie to McCluskey re: Recognition for Dr. Rentrop".

Appeal Record Page Nos. A04066–A04066 "Plaintiff's Trial Exh. No. PX–56. Email from Bossie to Reiser re: Agreement for Dr. Rentrop".

Appeal Record Page Nos. A04067–A04067 "Plaintiff's Trial Exh. No. PX–57. Harlan Daytimer Entry".

Appeal Record Page Nos. A04068–A04068 "Plaintiff's Trial Exh. No. PX–58. Letter from Bossie to Dr. Rentrop re: Recognition for Dr. Rentrop".

Appeal Record Page Nos. A04069–A04070 "Plaintiff's Trial Exh. No. PX–59. Taylor Daytimer Entry".

Appeal Record Page Nos. A04071–A04071 "Plaintiff's Trial Exh. No. PX–60. Letter from Taylor To Dr. Rentrop re: Abstract".

Appeal Record Page Nos. A04072–A04073 "Plaintiff's Trial Exh. No. PX–61. Taylor Daytimer Entry".

Appeal Record Page Nos. A04074–A04074 "Plaintiff's Trial Exh. No. PX–62. Letter From Childs To Dr. Rentrop re: Proposing Consulting Agreement".

Appeal Record Page Nos. A04075–A04075 "Plaintiff's Trial Exh. No. PX–63. Letter from Largey To Dr. Rentrop re: Colorado Calendar".

Appeal Record Page Nos. A04076–A04076 "Plaintiff's Trial Exh. No. PX–64. Taylor Daytimer Entry".

Appeal Record Page Nos. A04077–A04077 "Plaintiff's Trial Exh. No. PX–65. Taylor Daytimer Entry".

Appeal Record Page Nos. A04078–A04079 "Plaintiff's Trial Exh. No. PX–66. Taylor Daytimer Entry".

Appeal Record Page Nos. A04080–A04080 "Plaintiff's Trial Exh. No. PX–67. Letter from Kerker to Dr. Rentrop re: Rotterdam".

Appeal Record Page Nos. A04081–A04085 "Plaintiff's Trial Exh. No. PX–68. Harlan Lab Notebook Entry".

Appeal Record Page Nos. A04086–A04086 "Plaintiff's Trial Exh. No. PX–69. Harlan Lab Notebook Entry".

Appeal Record Page Nos. A04087–A04088 "Plaintiff's Trial Exh. No. PX–70. Letter from Taylor to Dr. Rentrop re: Required Testing for FDA PMAS".

Appeal Record Page Nos. A04089–A04090 "Plaintiff's Trial Exh. No. PX–71. Letter from Taylor to Dr. Rentrop re: Site for IDE".

Appeal Record Page Nos. A04091–A04091 "Plaintiff's Trial Exh. No. PX–72. Letter from Taylor to Dr. Rentrop re: Evaluate Track and Wire Movement".

Appeal Record Page Nos. A04092–A04093 "Plaintiff's Trial Exh. No. PX–73. Memorandum re: Process Changes to TA Package for Better Wire Movement".

Appeal Record Page Nos. A04094–A04095 "Plaintiff's Trial Exh. No. PX–74. Taylor Daytimer Entry".

Appeal Record Page Nos. A04096–A04096 "Plaintiff's Trial Exh. No. PX–75. Taylor Daytimer Entry".

Appeal Record Page Nos. A04097–A04097 "Plaintiff's Trial Exh. No. PX–76. Letter from Largey to Dr. Rentrop re: XTO Catheter Development".

Appeal Record Page Nos. A04098–A04098 "Plaintiff's Trial Exh. No. PX–77. Taylor Daytimer Entry".

Appeal Record Page Nos. A04099–A04099 "Plaintiff's Trial Exh. No. PX–78. Taylor Daytimer Entry".

Appeal Record Page Nos. A04100–A04100 "Plaintiff's Trial Exh. No. PX–79. Taylor Daytimer Entry".

Appeal Record Page Nos. A04101–A04102 "Plaintiff's Trial Exh. No. PX–80. Taylor Daytimer Entry".

Appeal Record Page Nos. A04103–A04103 "Plaintiff's Trial Exh. No. PX–81. Letter from Taylor to Dr. Rentrop re: Kink in Catheter".

Appeal Record Page Nos. A04104–A04104 "Plaintiff's Trial Exh. No. PX–82. Taylor Daytimer Entry".

Appeal Record Page Nos. A04105–A04105 "Plaintiff's Trial Exh. No. PX–83. Memo re: Catheter Evaluation by Dr. Rentrop".

Appeal Record Page Nos. A04106–A04107 "Plaintiff's Trial Exh. No. PX–84. Letter from Spectranetics to Dr. Rentrop re: Evaluating Catheters and Dr. Rentrop's Comments".

Appeal Record Page Nos. A04108–A04109 "Plaintiff's Trial Exh. No. PX–85. Letter from Taylor to Dr. Rentrop re: Evaluating Catheters and Dr. Rentrop's Comments".

Appeal Record Page Nos. A04110–A04111 "Plaintiff's Trial Exh. No. PX–86. Taylor Daytimer Entry".

Appeal Record Page Nos. A04112–A04113 "Plaintiff's Trial Exh. No. PX–87. Harlan Lab Notebook Entry".

Appeal Record Page Nos. A04114–A04114 "Plaintiff's Trial Exh. No. PX–88. Letter from Harlan to Dr. Brechfeld re: Catheter Performance".

Appeal Record Page Nos. A04115–A04115 "Plaintiff's Trial Exh. No. PX–89. Letter from Taylor to Dr. Brechfeld re: Review of Extreme XTO Protocol Summary".

Appeal Record Page Nos. A04116–A04116 "Plaintiff's Trial Exh. No. PX–90. Harlan Daytimer Entry".

Appeal Record Page Nos. A04117–A04117 "Plaintiff's Trial Exh. No. PX–91. Taylor Daytimer Entry".

Appeal Record Page Nos. A04118–A04118 "Plaintiff's Trial Exh. No. PX–92. Harlan Lab Notebook Entry".

Appeal Record Page Nos. A04119–A04120 "Plaintiff's Trial Exh. No. PX–93. Taylor Daytimer Entry".

Appeal Record Page Nos. A04121–A04121 "Plaintiff's Trial Exh. No. PX–94. Taylor Daytimer Entry".

Appeal Record Page Nos. A04122–A04123 "Plaintiff's Trial Exh. No. PX–95. Taylor Daytimer Entry".

Appeal Record Page Nos. A04124–A04125 "Plaintiff's Trial Exh. No. PX–96. Taylor Daytimer Entry".

Appeal Record Page Nos. A04126–A04127 "Plaintiff's Trial Exh. No. PX–97. Taylor Daytimer Entry".

Appeal Record Page Nos. A04128–A04129 "Plaintiff's Trial Exh. No. PX–98. Letter from Kevin Taylor to Dr. Hilton re: Product Specifications for New Products".

Appeal Record Page Nos. A04130–A04132 "Plaintiff's Trial Exh. No. PX–99. Letter from Dr. Hilton to Dr. Freeland re: Request for Permission To Use Catheters in Canada".

Appeal Record Page Nos. A04133–A04134 "Plaintiff's Trial Exh. No. PX–100. Taylor Daytimer Entry".

Appeal Record Page Nos. A04135–A04135 "Plaintiff's Trial Exh. No. PX–101. Harlan Lab Notebook Entry".

Appeal Record Page Nos. A04136–A04137 "Plaintiff's Trial Exh. No. PX–102. Taylor Daytimer Entry".

Appeal Record Page Nos. A04138–A04138 "Plaintiff's Trial Exh. No. PX–103. Taylor Daytimer Entry".

Appeal Record Page Nos. A04139–A04139 "Plaintiff's Trial Exh. No. PX–104. Taylor Daytimer Entry".

Appeal Record Page Nos. A04140–A04183 "Plaintiff's Trial Exh. No. PX–105. Trademark Agreements".

Appeal Record Page Nos. A04260–A04261 "Plaintiff's Trial Exh. No. PX–106. Letter from Nyce to re: Supplemental PMA application".

Appeal Record Page Nos. A04262–A04265 "Letter from Callahan to Quinn re: FDA".

Appeal Record Page Nos. A04266–A04270 "Letter from Nyce to FDA re: Amendment to PMA Supplement Application".

Appeal Record Page Nos. A04271–A04274 "Memo from Taylor re: Publication: Early X80 Experience and the Publication".

Appeal Record Page Nos. A04275–A04279 "Memo from Harlan re: Rational for not providing a Clinical Report".

Appeal Record Page Nos. A04280–A04284 "Plaintiff's Trial Exh. No. PX–107. Letter from Childs to Dr. Rentrop re: Patent Pending".

Appeal Record Page Nos. A04285–A04285 "Letter from Dr. Rentrop to Ross re: '125 Patent Issued".

Appeal Record Page Nos. A04286–A04287 "Letter from Hess to Schulte re: Patent License".

Appeal Record Page Nos. A04288–A04312 "Letter from Rader to Hess re: Colorado Complaint and attached Complaint".

Appeal Record Page Nos. A04313–A04329 "Order Granting Motion to Dismiss Colorado Action".

Appeal Record Page Nos. A04381–A04381 "Plaintiff's Trial Exh. No. PX–108. Final Catheter Assembly 80/80 Extreme XTO Drawing".

Appeal Record Page Nos. A04382–A04382 "Plaintiff's Trial Exh. No. PX–109. Final Catheter Assembly Vitesse .9mm Drawing".

Appeal Record Page Nos. A04383–A04383 "Plaintiff's Trial Exh. No. PX–110. Final Catheter Assembly 0.014 DR XTO Drawing".

Appeal Record Page Nos. A04384–A04384 "Plaintiff's Trial Exh. No. PX–111. Final Catheter Assembly Extreme .9mm".

Appeal Record Page Nos. A04385–A04393 "Plaintiff's Trial Exh. No. PX–112. Spectranetics Model 110–002 Instructions for Use".

Appeal Record Page Nos. A04394–A04399 "Spectranetics Model 110–001 Instructions for Use".

Appeal Record Page Nos. A04400–A04405 "Plaintiff's Trial Exh. No. PX–113. Spectranetics Model 110–004 Instructions for Use".

Appeal Record Page Nos. A04406–A04414 "Spectranetics Model 110–003 Instructions for Use".

Appeal Record Page Nos. A04415–A04418 "Plaintiff's Trial Exh. No. PX–114. Spectranetics Website Information re: .9mm Catheters".

Appeal Record Page Nos. A04419–A04420 "Plaintiff's Trial Exh. No. PX–115. Figure 1 of the '064 Patent".

Appeal Record Page Nos. A04421–A04421 "Plaintiff's Trial Exh. No. PX–116. Figure 2 of the '064 Patent".

Appeal Record Page Nos. A04422–A04422 "Plaintiff's Trial Exh. No. PX–117. Claim 1 of the '064 Patent".

Appeal Record Page Nos. A04423–A04423 "Plaintiff's Trial Exh. No. PX–118. Claim 8 of the '064 Patent".

Appeal Record Page Nos. A04425–A04425 "Plaintiff's Trial Exh. No. PX–120. Hoop Assembly Extreme XTO Drawing".

Appeal Record Page Nos. A04428–A04428 "Plaintiff's Trial Exh. No. PX–123. Page from '064 Prosecution History where Examiner Cites the German Patent Application".

Appeal Record Page Nos. A04429–A04429 "Plaintiff's Trial Exh. No. PX–124. 35 U.S.C. 282".

Appeal Record Page Nos. A04430–A04448 "Plaintiff's Trial Exh. No. PX–125. U.S. Patent No. 5,514,128".

Appeal Record Page Nos. A04449–A04466 "Plaintiff's Trial Exh. No. PX–126. U.S. Patent No. 5,643,251".

Appeal Record Page Nos. A04467–A04467 "Plaintiff's Trial Exh. No. PX–127. Prima 0.018".

Appeal Record Page Nos. A04468–A04469 "Plaintiff's Trial Exh. No. PX–128. AIS 1.32 Excimer Laser Model PC4017".

Appeal Record Page Nos. A04470–A04470 "Plaintiff's Trial Exh. No. PX–129. Eclipse 1.2mm Laserprime".

Appeal Record Page Nos. A04471–A04471 "Plaintiff's Trial Exh. No. PX–130. 1995 Spectranetics Laserwire 0.35" Outer Diameter".

Appeal Record Page Nos. A04472–A04482 "Plaintiff's Trial Exh. No. PX–131. Article by Dr. Cornelis A. F. Fulleken".

Appeal Record Page Nos. A04483–A04493 "Plaintiff's Trial Exh. No. PX–132. U.S. Patent No. 5,263,952".

Appeal Record Page Nos. A04494–A04506 "Plaintiff's Trial Exh. No. PX–133. U.S. Patent No. 5,429,617".

Appeal Record Page Nos. A04507–A04511 "Plaintiff's Trial Exh. No. PX–134. Marketing Statement XTO Devices".

Appeal Record Page Nos. A04512–A04515 "Plaintiff's Trial Exh. No. PC–135. Marketing Stattement XTO design".

Appeal Record Page Nos. A04516–A04519 "Plaintiff's Trial Exh. No. PX–136. Marketing Statement XTO design".

Appeal Record Page Nos. A04520–A04520 "Plaintiff's Trial Exh. No. PX–137. Project Goals and Strategies: Vitesse XTO Catheter".

Appeal Record Page Nos. A04521–A04522 "Plaintiff's Trial Exh. No. PX–138. Spectranetics Smallest Laser Angioplasty catheter for tortuous hard–to–treat lesions receives approval in Europe".

Appeal Record Page Nos. A04523–A04523 "Plaintiff's Trial Exh. No. PX–139. Point 9 Sales Forecast".

Appeal Record Page Nos. A04524–A04524 "Plaintiff's Trial Exh. No. PX–140. .9mm Catheter Budget for 2001".

Appeal Record Page Nos. A04525–A04531 "Plaintiff's Trial Exh. No. PX–141. Extreme/Vitesse Point .9mm Pre Market Approval Supplement".

Appeal Record Page Nos. A04532–A04532 "Plaintiff's Trial Exh. No. PX–142. Spectanetics' Press Announcement—"FDA Panel to Review Data on SPNC's LACI Trial on Oct. 2"".

Appeal Record Page Nos. A04533–A04574 "Plaintiff's Trial Exh. No. PX–143. The Spectranetics Corporation .9 Catheter Sales Sep. 2002–Sep. 2004".

Appeal Record Page Nos. A04575–A04575 "Plaintiff's Trial Exh. No. PX–144. The Spectranetics Corporation .9 Catheter Sales YTD Aug. 2004".

Appeal Record Page Nos. A04576–A04576 "Plaintiff's Trial Exh. No. PX–145. Low Profile Eccentric Catheter Screen Shot".

Appeal Record Page Nos. A04577–A04577 "Plaintiff's Trial Exh. No. PX–146. .014" Double Row Laser Support Catheter Drawing".

Appeal Record Page Nos. A04578–A04578 "Plaintiff's Trial Exh. No. PX–147. .014" Laser Support Catheter Drawing".

Appeal Record Page Nos. A04579–A04579 "Plaintiff's Trial Exh. No. PX–148. .018 Laser Support Catheter Drawing".

Appeal Record Page Nos. A04580–A04580 "Plaintiff's Trial Exh. No. PX–149. Harlan Lab Notebook Entry".

Appeal Record Page Nos. A04581–A04608 "Plaintiff's Trial Exh. No. PX–150. Article by Michele M. Riley "A Review of Court Awarded Royalty Rates in Patent Infringement Cases (1990–2001) (New)"".

Appeal Record Page Nos. A04641–A04641 "Plaintiff's Trial Exh. No. PX–151. Press Release "Spectranetics Receives FDA Approval to Market Its Smallest Point 9TM Catheters With Higher Laser Parameters"".

Appeal Record Page Nos. A04644–A04664 "Plaintiff's Trial Exh. No. PX–154. Export Report of Carl G. Degan".

Appeal Record Page Nos. A04665–A04891 "Plaintiff's Trial Exh. No. PX–155. Export Report of Christopher Reiser".

Appeal Record Page Nos. A04892–A04921 "Plaintiff's Trial Exh. No. PX–156. Expert Report of J. Ralph King".

Appeal Record Page Nos. A04922–A05051 "Plaintiff's Trial Exh. No. PX–157. Form 10–K Annual Report for year ended Dec. 31,2003, The Spectranetics Corporation".

Appeal Record Page Nos. A05052–A05052 "Plaintiff's Trial Exh. No. PX–158. Spectranetics Extreme/Vitesse .9mm Pre–Market Approval Supplement".

Appeal Record Page Nos. A05059–A05435 "Plaintiff's Trial Exh. No. PX–165. Certified copy of 6,673,064 Patent Prosecution History".

Appeal Record Page Nos. A08059–A08075 "Plaintiff's Trial Exh. No. PX–167. DX–9 (K) Order Granting Motion to Dismiss Complaint in Colorado".

Appeal Record Page Nos. A08081–A08086 "Plaintiff's Trial Exh. No. PX–174. Article—"Dependence of the XeCL Laser Cut Rate of Plaque on the Degree of Calcification, Laser Fluence, and Optical Pulse Duration," Lasers in Surgery and Medicine 10:414–419 (1990)".

Appeal Record Page Nos. A08087–A08093 "Plaintiff's Trial Exh. No. PX–175. Jul. 8, 1999 Fax from Kevin Taylor to Rentrop re Trademark Assignment Agreement".

Appeal Record Page Nos. A08095–A08102 "Plaintiff's Trial Exh. No. PX–177. Article—"Next Generation Catheters for Excimer Laser Coronary Angioplasty," Lasers Med Sci 2001,16:133–140 by K. Taylor and C. Reiser".

Appeal Record Page Nos. A08103–A08119 "Plaintiff's Trial Exh. No. PX–179. Spectranetics' Response to Plaintiff's Trial Subpoena".

Appeal Record Page Nos. A08121–A08121 "Plaintiff's Trial Exh. No. PX–182. Drawing (310–154) of Final Catheter Assembly Vitesse .9mm 80/80 150 cm, Continuous On".

Appeal Record Page Nos. A08122–A08122 "Plaintiff's Trial Exh. No. PX–183. Drawing (310–152) of Final Catheter Assembly 80/80 Extreme .9mm, 150 cm, Continuous On".

Appeal Record Page Nos. A08131–A08131 "Plaintiff's Trial Exh. No. PX–192. Spectranetics Sales (Page from PX–179)".

Appeal Record Page Nos. A08152–A08159 "Plaintiff's Trial Exh. No. PX–195. Nov. 18, 1999 Letter from Guy Childs to Rentrop re Consulting Agreement".

Appeal Record Page Nos. A08160–A08225 "Plaintiff's Trial Exh. No. PX–196. Spectranetics 10–K for year 1999".

Appeal Record Page Nos. A08226–A08311 "Plaintiff's Trial Exh. No. PX–197. Spectranetics 10–K for year 2000".

Appeal Record Page Nos. A08312–A08318 "Plaintiff's Trial Exh. No. PX–198. Aug. 31, 1999 Letter from Guy Childs to Rentrop re Trademark Assignment Agreement".

Appeal Record Page Nos. A08319–A08324 "Plaintiff's Trial Exh. No. PX–200. Spectranetics Annual Report for year 2003".

Appeal Record Page Nos. A08325–A08325 "Plaintiff's Trial Exh. No. PX–201. Page from Ken Harlan's Lab Notebook dated Oct. 8, 1999".

Appeal Record Page Nos. A09081–A09086 "Defendant The Spectranetics Corporation's Brief in Support of its Motion for Directed Verdict Pursuant to Fed. R. Civ. P. 50 Dismissing Dr. Rentrop's Claim for Willful Infringement, and all attachments thereto".

Appeal Record Page Nos. A09087–A09093 "Plaintiffs Opposition to Defendant The Spectranetics Corporation's Brief in Support of Its Motion for Directed Verdict Pursuant to Fed. R. Civ. P. 50 Dismissing Dr. Rentrop's Claim for Willful Infringement and all attachments thereto".

Appeal Record Page Nos. A09187–A09193 "The Spectranetics Corporation's Brief in Support of Its Renewed and Supplemented Motion for Directed Verdict Pursuant to Fed. R. Civ. P. 50 Dismissing Dr. Rentrop's Claim for Willful Infringement".

Appeal Record Page Nos. A09194–A09196 "Letter to Judge Castel from Glenn Forbis re entry of directed verdict of non–infringement".

Appeal Record Page Nos. A09197–A09232 "Spectranetics' Renewed Motion Pursuant to Fed. R. Civ. P. 50 of Non–Infringement, Brief in Support, and all attachments thereto".

Appeal Record Page Nos. A09233–A09271 "Plaintiff's Opposition to Spectranetics' Renewed Motion Pursuant to Fed. R. Civ. P. 50 of Non–Infringement, Brief in Support, and all attachments thereto".

Appeal Record Page Nos. A09272–A09278 "Spectranetics' Reply Brief in Support of Its Renewed Motion Pursuant to Fed. R. Civ. P. 50 of Non–Infringement, and all attachments thereto".

Appeal Record Page Nos. A09279–A09292 "Spectranetics' Motion Pursuant to Fed. R. Civ. P. 59 and 60 to Amend the Jury's Verdict With Respect to Damages & Brief in Support, and all attachments thereto".

Appeal Record Page Nos. A09293–A09325 "Plaintiffs Opposition to Spectranetics' Motion Pursuant to Fed. R. Civ. P. 59 and 60 to Amend the Jury's Verdict With Respect to Damages & Brief in Support, and all attachments thereto."

Appeal Record Page Nos. A09326–A09340 "Spectranetics' Reply Brief in Support of Its Motion Pursuant to Fed. R. Civ. P. 59 and 60 to Amend the Jury's Verdict With Respect to Damages, and all attachments thereto."

Appeal Record Page Nos. A09341–A09402 "Defendant Spectranetics' Proposed Findings of Fact and Conclusions of Law for Inequitable Conduct, and all attachments thereto".

Appeal Record Page Nos. A09403–A09484 "Plaintiffs Response to Defendant Spectranetics' Proposed Findings of Fact and Conclusions of Law for Inequitable Conduct, and all attachments thereto".

Appeal Record Page Nos. A09485–A09661 "Defendant Spectranetics' Proposed Findings of Fact and Conclusions of Law in Support of Its Affirmative Defense of Implied License, and all attachments thereto".

Appeal Record Page Nos. A09662–A09750 "Plaintiffs Response to Defendant Spectranetics' Proposed Findings of Fact and Conclusions of Law in Support of Its Affirmative Defense of Implied License, and all attachments thereto".

Appeal Record Page Nos. A09751–A09786 "Plaintiff's Proposed Findings Of Fact And Conclusions Of Law Regarding the Defenses of Implied–In–Law License and Inequitable Conduct".

Appeal Record Page Nos. A09787–A09952 "Spectranetics' Response to Plaintiff's Proposed Findings of Fact and Conclusions of Law Regarding the Defenses of Implied–in–Law License and Inequitable Conduct, and all attachments thereto".

Appeal Record Page Nos. A09953–A09960 "Spectranetics' Motion to Preclude Plaintiff from Seeking Pre– and Post–Judgment Interest and from Seeking a Premature Entry of Judgment & Brief in Support, and all attachments thereto".

Appeal Record Page Nos. A09961–A09966 "Plaintiffs Opposition to Spectranetics' Motion to Preclude Plaintiff from Seeking Pre–and Post–Judgment Interest and from Seeking a Premature Entry of Judgment & Brief in Support, and all attachments thereto".

Appeal Record Page Nos. A09967–A09971 "Spectranetics Reply Brief in Support of Its Motion to Preclude Plaintiff from Seeking Pre– and Post–Judgment Interest and from Seeking a Premature Entry of Judgment, and all attachements thereto".

Joint Pretrial Order.

Deposition of Kenneth D. Harlan, vol. I, Sep. 22, 2004.

Deposition of Christopher Reiser, Sep. 21, 2004.

Deposition of Dr. Peter Rentrop, Sep. 28, 2004.

Deposition of Kevin D. Taylor, vol. I, Sep. 20, 2004.

Deposition of Kevin D. Taylor, vol. II, Dec. 14, 2004.

Rule 30(b)(6) Deposition of Guy A. Childs, Sep. 23, 2004.

Deposition of Kenneth D. Harlan, vol. II, Dec. 13, 2004.

Decision, The Spectranetics Corporation, in *Dr. Peter Rentrop v. The Spectranetics Corporation*, U.S.C.A. for the Federal Circuit, Appeal No. 2007–1560, Dec. 18, 2008.

Apr. 29, 2005. Transcript of Markman Hearing in the *Peter Rentrop v. The Spectranetics Corporation*, 04 civ 101 (S.D.N.Y 2005).

Order denying Summary Judgment Motion of The Spectranetics Corporation in *Peter Rentrop v. The Spectranetics Corporation*, 04 civ 101 (S.D.N.Y 2005).

Memorandum of Law in Support of Plaintiffs' Motions in Limine.

Defendant Memorandum of Law in Opposition to Plaintiff Rentrop's Motions in Limine.

Brief for Plaintiff–Appellee, Dr. Peter Rentrop, in *Dr. Peter Rentrop v. The Spectranetics Corporation*, U.S.C.A for the Federal Circuit, Appeal No. 2007–1560, Apr. 28, 2008.

Reply Brief of Defendant–Appellant, The Spectranetics Corporation, in *Dr. Peter Rentrop v. The Spectranetics Corporation*, U.S.C.A for the Federal Circuit, Appeal No. 2007–1560, May 27, 2008.

Rebuttal to Expert Report of Christopher Reiser, Ph.D. and Expert Report by Edward Sinofsky, PhD, Apr. 13, 2005.

Expert Witness Report of James D. Woods, Ph. D., Jan. 28, 2005.

Rebuttal Expert Witness Report of James D. Woods. Ph. D., Apr. 14, 2005.

Appeal Record Page Nos. A02854.01–A02854.01 "Defendant's Trial Exh. No. Q4. Page 152 from book "Intellectual Property Infringement Damages: A Litigation Support Handbook 2003 Cumulative Supplement" by Russell L. Parr".

Appeal Record Page Nos. A03893–A03893 "Plaintiff's Trial Exh. No. PX–6. Progression of tools video".

Appeal Record Page Nos. A03894–A03894 "Plaintiff's Trial Exh. No. PX–7. Intervention Video".

Appeal Record Page Nos. A03895–A03895 "Plaintiff's Trial Exh. No. PX–8. Demonstrative of blocked artery in the heart".

Appeal Record Page Nos. A08076–A08076 "Plaintiff's Trial Exh. No. PX–168. Physical Sample of Point 9 Vitesse (rapid exchange) Excimer Laser Catheter".

Appeal Record Page Nos. A08077–A08077 "Plaintiff's Trial Exh. No. PX–169. Physical Sample of Point 9 X80 Vitesse (rapid exchange) Excimer Laser Catheter".

Appeal Record Page Nos. A08078–A08078 "Plaintiff's Trial Exh. No. PX–170. Physical Sample of Point 9 Extreme (over–the–wire) Excimer Laser Catheter".

Appeal Record Page Nos. A08079–A08079 "Plaintiff's Trial Exh. No. PX–171. Physical Sample of Point 9 X80 Extreme (over–the–wire) Excimer Laser Catheter".

Appeal Record Page Nos. A08080–A08080 "Plaintiff's Trial Exh. No. PX–172. Physical Sample of 1.4 Concentric Excimer Laser Ablation Catheter".

Appeal Record Page Nos. A08094–A08094 "Plaintiff's Trial Exh. No. PX–176. Physical sample of Judkins Catheter".

Appeal Record Page Nos. A08120–A08120 "Plaintiff's Trial Exh. No. PX–181. Physical Sample of .9 X80 Turbo RX".

Appeal Record Page Nos. A08127–A08127 "Plaintiff's Trial Exh. No. PX–188. Three Instruction Manuals for ELCA, CLIR Path and .9 X80 ELCA".

Appeal Record Page Nos. A08128–A08128 "Plaintiff's Trial Exh. No. PX–189. Spectranetics Sales (PowerPoint Slide of SPE 10256/PX–179)".

Appeal Record Page Nos. A08132–A08151 "Plaintiff's Trial Exh. No. PX–194. Sep. 22, 1999 Letter from Guy Childs to Rentrop re Consulting Agreement".

Opinion, Dr. Peter Rentrop, Plaintiff—against The Spectranetics Corporation, Defendant, 2007 U.S. Dist. Lexis 87326 (U.S. District Court for the Southern District of New York, Nov. 26, 2007).

Opinion, Dr. Peter Rentrop, Plaintiff—against The Spectranetics Corporation, Defendant, 2005 U.S. Dist. Lexis 290 (U.S. District Court for the Southern District of New York, Jan. 7, 2005).

Opinion, Dr. Peter Rentrop, Plaintiff—against The Spectranetics Corporation, Defendant, 2004 U.S. Dist. Lexis 10312(U.S. District Court for the Southern District of New York Jun. 4, 2004).

Plaintiff's Trial Exh. No. PX–173. Physical Sample of Laser Sheath.

Plaintiff's Trial Exh. No. PX–180. Physical Sample of Turbo 0.9 Over–the–Wire Excimer Laser Catheter.

Brief of Defendant–Appellant, The Spectranetics Corporation, in *Dr. Peter Rentrop v. The Spectranetics Corporation*, U.S.C.A for the Federal Circuit, Appeal No. 2007–1560, May 27, 2008.

Henson, Kenneth D., MD, et al., "Treatment Of Refractory Coronary Occlusions With A New Excimer Laser Catheter: Preliminary Clinical Observations," Coronary Artery Disease 1993, vol. 4, No. 11, pp. 1001–1006.

Hamburger, Jaap N., MD, et al., "Recanalization Of Chronic Total Coronary Occlusions Using A Laser Guide Wire: A Pilot Study," JACC vol. 30, No. 3, pp. 649–656, Sep. 1997.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–16 is confirmed.

* * * * *